US007098174B2

(12) United States Patent
Takemura et al.

(10) Patent No.: US 7,098,174 B2
(45) Date of Patent: Aug. 29, 2006

(54) SLIME REMOVER AND SLIME PREVENTING/REMOVING AGENT

(75) Inventors: Eiji Takemura, Tokyo (JP); Izumi Takano, Tokyo (JP); Kaoru Muto, Chiba (JP); Takashi Yoshihara, Chiba (JP); Akira Doshida, Chiba (JP)

(73) Assignee: Nippon Soda Co., Ltd., Tokyo (JP)

( * ) Notice: Subject to any disclaimer, the term of this patent is extended or adjusted under 35 U.S.C. 154(b) by 78 days.

(21) Appl. No.: 11/022,724

(22) Filed: Dec. 27, 2004

(65) Prior Publication Data

US 2005/0103709 A1    May 19, 2005

Related U.S. Application Data

(62) Division of application No. 10/252,150, filed on Sep. 20, 2002, now Pat. No. 6,927,199, which is a division of application No. 09/763,538, filed as application No. PCT/JP99/04732 on Sep. 1, 1999, now Pat. No. 6,528,467.

(30) Foreign Application Priority Data

| Sep. 1, 1998 | (JP) | ............................... 10-246807 |
| Sep. 4, 1998 | (JP) | ............................... 10-251392 |
| Mar. 2, 1999 | (JP) | ............................... 11-54253 |
| Mar. 18, 1999 | (JP) | ............................... 11-73688 |

(51) Int. Cl.
*C11D 3/48* (2006.01)

(52) U.S. Cl. ...................... 510/195; 510/191; 510/199; 510/382; 510/391; 510/445; 510/446; 510/447; 4/222; 4/222.1; 4/222.6

(58) Field of Classification Search ................ 510/195, 510/191, 199, 382, 391, 445, 446, 447; 4/222, 4/222.1, 226.1
See application file for complete search history.

(56) References Cited

U.S. PATENT DOCUMENTS

| 852,044 | A |   | 4/1907  | Van Der Minden |           |
| 1,916,357 | A |   | 7/1933  | Brownstein |             |
| 2,087,592 | A |   | 7/1937  | Chestnut |               |
| 2,723,905 | A |   | 11/1952 | Coakley |                |
| 3,112,499 | A |   | 12/1963 | Thornton |               |
| 3,597,772 | A |   | 8/1971  | Leavitt et al. |         |
| 4,644,021 | A | * | 2/1987  | Toda et al. | 523/122 |
| 4,780,317 | A | * | 10/1988 | Sekikawa et al. | 424/468 |
| 4,818,771 | A | * | 4/1989  | Toda et al. | 514/616 |
| 5,079,000 | A | * | 1/1992  | Takahashi et al. | 424/742 |
| 5,165,119 | A |   | 11/1992 | Yamato |                 |
| 5,382,571 | A | * | 1/1995  | Granger et al. | 514/58 |
| 5,523,020 | A | * | 6/1996  | Yagi et al. | 252/404 |
| 5,637,308 | A |   | 6/1997  | Del Corral et al. |       |
| 6,030,636 | A | * | 2/2000  | Randolph et al. | 424/426 |

FOREIGN PATENT DOCUMENTS

| EP | 0 423 391 A1 | 4/1991 |
| EP | 0 648 415 A2 | 4/1995 |
| JP | 64-40408     | 2/1989 |
| JP | 6046069      | 2/1994 |
| JP | 07-148498    | 6/1995 |
| JP | 7-184823     | 7/1995 |
| JP | 7184823      | 7/1995 |
| JP | 07-304604    | 11/1995 |
| JP | 08-053304    | 2/1996 |
| JP | 8-113502     | 5/1996 |
| JP | 08-113502    | 5/1996 |
| JP | 8113502      | 5/1996 |
| JP | 8128090      | 5/1996 |
| JP | 08-1513103   | 6/1996 |
| JP | 8157305      | 6/1996 |
| JP | 8158441      | 6/1996 |
| JP | 8-270037     | 10/1996 |
| JP | 8268818      | 10/1996 |
| JP | 8270037      | 10/1996 |
| JP | 08270037     | 10/1996 |
| JP | 9000292      | 1/1997 |
| JP | 9-31495      | 2/1997 |
| JP | 9030915      | 2/1997 |
| JP | 9031495      | 2/1997 |
| JP | 9-124423     | 5/1997 |
| JP | 9124422      | 5/1997 |
| JP | 9124423      | 5/1997 |
| JP | 9154923      | 6/1997 |
| JP | 9194313      | 7/1997 |

(Continued)

*Primary Examiner*—Charles Boyer
(74) *Attorney, Agent, or Firm*—Dennis G. LaPointe

(57) ABSTRACT

A drainage slime remover capable of spreading a solution of a solid over slime generated wall surface portions, comprising a solid containing a microorganism growth retarding substance and a container which has a shape for permitting the installation thereof at the inlet or upper portion of a drain outlet and stores the solid, characterized in that the container has drain flow-in holes having an opening capable of controlling a drain flow-in amount and provided in the upper surface or the upper side portion of the container and solution flow-out holes having an opening capable of controlling a flow-out amount if a solid solution and provided in the bottom or the lower side portion of the container or additionally in the side surface thereof; and a slime preventing/removing agent which can remove slime from portions such as kitchen sinks and bathroom drain outlets where slime is grown by metabolites such as miscellaneous germs and mildews and which can prevent the occurrence of slime safely and for an extended period of time.

9 Claims, 14 Drawing Sheets

FOREIGN PATENT DOCUMENTS

| | | |
|---|---|---|
| JP | 9206040 | 8/1997 |
| JP | 9-227317 | 9/1997 |
| JP | 9227317 | 9/1997 |
| JP | 9-296492 | 11/1997 |
| JP | 9296492 | 11/1997 |
| JP | 09296492 | 11/1997 |
| JP | 10245306 | 9/1998 |
| JP | 10245308 | 9/1998 |
| JP | 11-043404 | 2/1999 |
| WO | WO 97/02744 | 1/1997 |

\* cited by examiner

SLIME REMOVER AND SLIME PREVENTING/REMOVING AGENT

RELATED APPLICATION

This application is a divisional application of Ser. No. 10/252,150 filed Sep. 20, 2002, now U.S. Pat. No. 6,927,199, which is a divisional of U.S. patent application Ser. No. 09/763,538, filed May 2, 2001, now U.S. Pat. No. 6,528,467, issued Mar. 4, 2003, which is a 35 USC 371 national stage application of PCT/JP99/04732 filed Sep. 1, 1999.

BACKGROUND OF THE INVENTION

1. Field of Invention

The present invention relates to a slime preventing/removing agent which is installed in a place where metabolites of miscellaneous germs, mildews and the like cause slime and bad smells, such as drain outlets of kitchen sinks, bathrooms and toilet floors, and is useful to remove slime, to prevent the occurrence of slime or to control slime. The present invention also relates to a slime remover and container for it, and a method of removing slime with them. The invention particularly relates to a slime remover for a garbage basket in a kitchen sink, of a type that the drain outlet of a household kitchen sink is made wider than the main drainpipe, a garbage basket is installed which collects garbage coming out together with drainage, such as cooking material wastes, and the remover is discarded when a certain amount of garbage is accumulated.

2. Background Art

It is known that the main ingredient of slime in the drain outlets of kitchen sinks and bathrooms is polysaccharides secreted by bacteria, when they use food materials, surface active agents, soaps, human dirt and others as nutrient sources.

It is so far well-known, as slime preventing chemicals for garbage baskets installed in the drain outlets of household kitchen sinks, that tablets, of which a chlorine-type oxidizing agent, such as trichloroisocyanuric acid, dichloroisocyanuric acid or bromochlorodimethylhydantoin, alone or its mixture with other ingredients is pressure molded, are stored in plastic nets or basket-shaped containers, and hung by strings or the like in garbage baskets for preventing the occurrence of slime in the baskets (Japanese Patent Laid-open No. Hei 8-128090). These chemicals have been marketed by trade names, such as "Slime Removing Agents", for practical use for the last few years.

Among the chemicals mentioned above, slime removing agents of bleaching powder type exhibit effects on the prevention of slime and bad smells of garbage baskets, thanks to the powerful sterilizing power of the active ingredient of a hypochlorite oxidizing agent, and are therefore used widely. Because of their powerful oxidizing power, garbage baskets and drainpipe materials around them become deteriorated or corroded, and poisonous chlorine gas is also generated. An amount of chlorine gas generated increases particularly when the agent reacts with an acidic substance, such as vinegar, causing a dangerous situation. Isocyanuric acid-type chemcials containing trichloroisocyanuric acid or the like as the active ingredient have safety problems such that their contact with alkaline or sodium-hypochlorite detergents generates gas with irritating smells, such as explosive nitrogen trichloride.

To solve the above problems, there have been proposed a variety of "slime removing agents" using germicides other than chlorine-type oxidizing agents. For example, those known are peroxides such as sodium percarbonates, potassium persulfate and sodium perborate (Japanese Patents Laid-open Nos. Hei 8-268818 and 9-31495), iodine-type germicides such as povidone iodine (Japanese Patents Laid-open Nos. Hei 9-124423 and 9-227317), chemicals composing sulfur compounds, such as sulfite, and chemicals for pasteurization (Japanese Patent Laid-open No. Hei 9-124422), volatile pasteurizing agents such as ortho-phenylphenol, diphenyl, 2-isopropyl-5-methylphenol and hinokitiol (Japanese Patent Laid-open No. Hei 9-206040), inorganic germicides of which silver ions, copper ions or the like are supported by inorganic compounds such as zeolite or silica gel (Japanese Patents Laid-open Nos. Hei 8-157305, 9-30915 and 9-194313), and tablets of which industrial germicides or the like, such as para-chloromethaxylenol, alone or with appropriate dissolution regulators added are pressure molded.

These "slime removing agents" using germicides other than chlorine-type oxidizing agents are stored in plastic nets or basket-shaped containers and hung by strings or other means in the garbage baskets, similar to the "slime removing agents" composing chlorine-type oxidizing agents. Some of the above agents are marketed as "slime removing agents" using no oxidizing agents of chlorine type. They have weaker sterilizing power than known "slime removing agents" containing chlorine-type oxidizing agents as the active ingredients do and insufficient preventive effects on slime and bad smells so as not to have become popular yet.

Japanese Patent Laid-open No. Hei 7-184823 has disclosed "slime removing agents" that an antimicrobial agent, such as a mixture of 5-chloro-2-methyl-4-isothiazolin-3-one and 2-methyl-4-isothiazolin-3-one, is supported by porous fine inorganic particles, such as hollow porous silica, and stored in a water-permeable bag, for example, made of nonwoven fabric, or supported by a water-soluble substance, such as protein or polysaccharide, and made film. 5-Chloro-2-methyl-4-isothiazolin-3-one has strong antimicrobial power and does not corrode materials or generates gas. However, it is easily soluble in water, so it has the disadvantage of a shorter shelf life than that of known chemicals. Besides, there is a safety issue when it is used in households due to severe skin irritation.

In addition to those mentioned above, known are devices having fixing sections to fix containers storing slime removing agents to garbage basket handles through the joints (Japanese Patent Laid-open No. Hei 9-292), types using garbage netting baskets coated with fluororesin (Japanese Patent Laid-open No. Hei 8-158441), devices jetting electrolytic, acidic, ionic water from circular pipes fixed around netting baskets (Japanese Publication No. of Utility Model Registration Hei 6-46069), and germ and mildew preventive devices supplying solutions having an action of preventing germs and mildews into the upper parts of inlet pipes (Japanese Patent Laid-open No. Hei 9-154923).

It is an object of the present invention to provide a drain slime remover that can be easily installed in the upper part of an inlet pipe, is excellent in safety and handling, and can spread the agent-dissolved solution from a container storing a slime preventing/removing agent with appropriate solubility over the wall surface of the drainpipe. It was found that a pressure molded product of an antimicrobial agent, particularly a clathrate compound of an antimicrobial agent and a multi-molecular host compound, with a specific base material is not dangerous, is excellent in safety and handling, retains appropriate solubility and has a slime preventing/removing effect. Thus the present invention has been completed.

DISCLOSURE OF THE INVENTION

The inventors of the present invention have proposed slime preventing/removing agents of non-bleaching powder type that a clathrate compound consisting of 5-chloro-2-methyl-4-isothiazolin-3-one and a multi-molecular host compound is pressure molded (Japanese Patent Application No. Hei 9-50384). The agents have reduced skin irritation and lowered water solubility, thanks to multi-molecular clathrate compounds of 5-chloro-2-methyl-4-isothiazolin-3-one with host compounds, and are thus excellent slime preventing/removing agents. The inventors of the present invention have also proposed slime preventing/removing agents prepared by the pressure molding of an organic iodine antimicrobial agent and a solid acid (Japanese Patent Application No. Hei 9-50385). These slime preventing/removing agents have also been confirmed to have excellent slime preventing/removing effects.

A chemical containing a chlorine-type oxidizing agent as an active ingredient sterilizes portions including where the chemical solution does not touch, by chlorine gas generated from the agent, even if it is installed in the bottom of a garbage basket. Therefore it is possible to prevent slime growth all over the inside of the basket. Contrary to it, a formulation containing an oxidizing agent of non-chlorine type as an active ingredient, particularly the aforementioned slime preventing/removing agent of the multi-molecular clathrate compound composing 5-chloro-2-methyl-4-isothiazolin-3-one with a host compound or a pressure-molded organic iodine antimicrobial agent, has a limitation of the excellent slime preventing/removing effects only on the surrounding of the formulation installed. Their effects are particularly weak on the upper part above the chemical installation site. With the above findings, various drain slime removers, with which these slime preventing/removing agents could be installed at the tops or upper parts of drainpipes and solutions of the said agents spread over the wall surface of the pipes and the like, were made on trial, and slime preventing/removing effects were studied. The effects of slime prevention and removal were confirmed to complete the present invention.

The present invention is directed to the following:

(1) A drain slime remover capable of spreading a solid-dissolved solution over slime contaminated wall surfaces, characterized in that it comprises a solid containing a microorganism growth retarding substance and a container which has a shape for permitting its installation at the top or upper part of an inlet pipe and stores the solid, and that the said container has drainage flow-in holes having an opening degree capable of controlling the drainage flow-in amount and provided in the upper surface or the upper side of the container and solution flow-out holes having an opening degree capable of controlling the flow-out amount of a solid-dissolved solution and provided in the bottom or the lower side, or additionally in the side, of the container.

(2) A drain slime remover according to (1), in which the container has a shape of a filter or integrated with a filter that is installed at the inlet pipe.

(3) A drain slime remover according to (1) or (2), in which the solution flow-out holes are provided in the bottom of the container, and in the sides at the peripheral and central sides of the inlet pipe.

(4) A drain slime remover according to (1) to (3), in which the solution flow-out holes have an opening degree capable of controlling the maximum amount of water held in the container to flow out at 0.5 to 500 seconds.

(5) A drain slime remover according to (1) to (4), in which the total opening area of the solution flow-out holes is 0.98 to 0.01 of that of the drainage flow-in holes.

(6) A drain slime remover according to (1) to (5), in which the drainage flow-in holes are made at least in the upper surface of the container and provided with two or more drainage flow-in slits composing one or more slits along the direction towards the center of the inlet pipe at appropriate intervals.

(7) A drain slime remover according to (6), in which the slits of the slit-shaped drainage flow-in holes are 0.5 to 4 mm wide.

(8) A drain slime remover according to (6) or (7), in which the slits are made in the upper surface of the container, reach the side end of the central part of the container towards the direction of the inlet pipe center, and further continuously cut up to the upper part at the center side.

(9) A drain slime remover according to (1) to (3), in which the drainage flow-in holes of the container are composed of hydrophilic nonwoven fabric.

(10) A drain slime remover according to (1) to (3), in which the drainage flow-in holes of the container have a netting structure.

(11) A drain slime remover according to (1) to (10), in which a chemical of non-bleaching powder type is used as the microorganism growth retarding substance.

(12) A drain slime remover according to (11), in which a clathrate compound composing 5-chloro-2-methyl-4-isothiazolin-3-one and a multi-molecular host compound is used as the chemical of non-bleaching powder type.

(13) A drain slime remover according to (11), in which an organic iodine antimicrobial agent is used as the chemical of non-bleaching powder type.

(14) A drain slime remover according to (1) to (13), in which two or more, same or different, solids of small granules less than 30 mm in the maximum length are used as the solid.

(15) A method of removing slime in a way that a container, in which solids containing a microorganism growth retarding substance are stored, is installed in the upper part of the slime contaminated wall surface, the solids are dissolved by drainage flowing in from drainage flow-in holes provided in the upper surface or upper side of the container, and the solid-dissolved solution flows out from solution flow-out holes provided in the bottom or the lower side, or additionally in the side, of the container in order to spread the solution over the slime contaminated wall surfaces.

(16) A container for removing slime, capable of spreading a solid-dissolved solution over slime contaminated wall surfaces, characterized in that the container has a shape for permitting its installation at the top or upper part of an inlet pipe, can store solids containing a microorganism growth retarding substance in the inside, and has flow-out holes for a solid-dissolved solution in the bottom or the lower side, or additionally in the side, and drainage flow-in holes in the upper surface or the upper side, and the total opening area of the solution flow-out holes is 0.98 to 0.01 of that of the drainage flow-in holes.

(17) A container for removing slime, capable of spreading a solid-dissolved solution over slime contaminated wall surfaces, characterized in that the container has a shape for permitting its installation at the top or upper part of an inlet pipe, can store solids containing a microorganism growth retarding substance in the inside, and has flow-out holes for a solid-dissolved solution in the bottom or the lower side, or additionally in the side, and drainage flow-in holes of slit type in the upper surface or the upper side with slits being 0.5 to 4 mm wide.

(18) A slime preventing/removing agent characterized in that an antimicrobial agent of non-bleaching powder type is pressure molded together with one or more base materials selected from calcium hydrogen phosphate dihydrate, tricalcium phosphate anhydride, magnesium hydrogen phosphate tri-hydrate, magnesium hydrogen phosphate octa-hydrate, lactose, vanillin, calcium citrate tetra-hydrate, calcium sulfate dihydrate, calcium sulfate hemi-hydrate, acetoacetate anilide, acetoacetate-o-toluidide, acetoacetate-p-toluidide, acetoacetate-o-anicidide, sorbitol, glycerin monofatty acid esters, alkylsorbitan esters (HLB: 14 or less) and sucrose fatty acid esters (HLB: 14 or less).

(19) A slime preventing/removing agent according to (18), in which the antimicrobial agent of non-bleaching powder type is a clathrate compound composing an antimicrobial agent and a multi-molecular host compound.

(20) A slime preventing/removing agent according to (19), in which the multi-molecular host compound is one or more compounds selected from the group consisting of the following compounds:

tetrakisphenols
1,1,6,6-tetraphenyl-2,4-hexadiyn-1,6-diol,
1,6-bis(2-chlorophenyl)1,6-diphenylhexan-2,4-diyn-1,6-diol,
1,1,4,4-tetraphenyl-2-butyn-1,4-diol,
2,5-bis(2,4-dimethylphenyl)hydroquinone,
1,1-bis(2,4-dimethylphenyl)-2-propyn-1-ol,
1,1,2,2-tetraphenylethan-1,2-diol,
1,1-bi-2-naphthol,
9,10-diphenyl-9,10-dihydroxyanthracene,
1,1,6,6-tetra(2,4-dimethylphenyl)-2,4-hexadiyn-1,6-diol,
9,10-bis(4-methylphenyl)-9,10-dihydroxyanthracene,
1,1-bis(4-hydroxyphenyl)cyclohexane, N,N,N',N'-tetrakis(cyclohexyl)-(1,1'-biphenyl)-2,2'-dicarboxyamide,
4,4'-sulfonylbisphenol,
4,4'-butylidenebis(3-methyl-6-tert-butylphenol),
2,2'-methylenebis(4-methyl-6-tert-butylphenol),
4,4'-thiobis(4-chlorophenol),
2,2'-methylenebis(4-chlorophenol),
deoxycholic acid,
cholic acid,
α, α, α', α'-tetraphenyl-1,1'-biphenyl-2,2'-dimethanol,
t-butylhydroquinone,
2,5-di-tert-butylhydroquinone,
granular corn starch,
1,4-diazabicyclo-(2,2,2)-octane,

(21) A slime preventing/removing agent according to (19) or (20), in which the antimicrobial agent of non-bleaching powder type is 5-chloro-2-methyl-4-isothiazolin-3-one.

(22) A slime preventing/removing agent according to (18), in which the antimicrobial agent of non-bleaching powder type is an organic iodine antimicrobial agent.

(23) A slime preventing/removing agent according to one of (18) to (22), in which calcium sulfate hemi-hydrate is β-type calcium sulfate hemi-hydrate.

(24) A slime preventing/removing agent according to one of (18) to (23), in which the slime preventing/removing agent contains a $C_{14}$ to $C_{24}$ saturated fatty acid as a dissolution regulator.

(25) A slime preventing/removing agent according to (24), in which the $C_{14}$ to $C_{24}$ saturated fatty acid is stearic acid or lauric acid.

(26) A small slime preventing/removing agent according to (18) to (25), in which the molded product is a tablet and the maximum length of the tablet is 15 mm or shorter.

(27) A slime removing method characterized in that a nonwoven fabric bag or a holed plastic film bag, that contains the small slime preventing/removing agent according to (26), or a flexible tape-shaped material carrying the small preventing/removing agents, is fixed on the surface or upper surface of slime contaminated wall, and the solution of the slime preventing/removing agent spreads over the wall.

As for substances to retard the growth of microorganisms, various known germicides and antimicrobial agents can be used in the present invention. All the common compounds known as mildew proofing agents or antibacterial agents, natural essential oils having antimicrobial activities and the like can be employed. However, those having wide antimicrobial spectra are preferred. Examples of chlorine chemicals include dichlorodimethylhydantoin, bromochlorodimethylhydantoin, sodium dichloroisocyanurate, potassium dichloroisocyanurate, hydrates (e.g., dihydrate) of sodium dichloroisocyanurate, hydrates of potassium dichloroisocyanurate, trichloroisocyanuric acid and sodium hypochlorite. Examples of non-chlorine chemicals include sodium percarbon, potassium persulfate, sodium perborate, ortho-phenylphenol, diphenyl, 2-isopropyl-5-methylphenol, para-chloromethaxylenol, n-butyl para-hydroxybenzoate, ethyl para-hydroxybenzoate, methyl para-hydroxybenzoate, benzalkonium chloride, benzethonium chloride, chlorohexidine hydrochloride, chlorohexidine gluconate, methylenebisthiocyanate, 2-pyridinethiol-1-oxide, zinc 2-pyridinethiol-1-oxide, sodium 2-pyridinethiol-1-oxide, N,N'-hexamethylenebis(4-carbamoyl-1-decylpyridinium bromide), 4,4'-(tetramethylenediamino)bis(1-decylpyridinium bromide) and 2-bromo-2-nitropropan-1,3-diol.

As for microorganism growth retarding substances of the present invention, clathrate compounds composing mildew proofing agents or antibacterial agents with multi-molecular host compounds can be advantageously used. When the clathrate compounds are used, examples of mildew proofing agents or antibacterial agents include 5-chloro-2-methyl-4-isothiazolin-3-one, 2-methyl-4-isothiazolin-3-one, 4,5-dichloro-3-n-octyl-isothiazolin-3-one, 1,2-benzisothiazolin-3-one, 2-methoxycarbonylbenzimidazole, 2,3,5,6-tetrachloro-4-methanesulfonylpyridine, 2-thiocyanomethybenzothiazole, 2,2-dithio-bis-(pyridin-1-oxide), 3,3,4,4-tetrahydrothiophene-1,1-dioxide, 4,5-dichloro-1,2-dithiolan-3-one, 5-chloro-4-phenyl-1,2-dithiolan-3-one, N-methylpyrolidone, phenyl-(2-cyano-2-chlorovinyl)sulfone, methylenebisthiocyanate, 2-bromo-2-nitropropane-1,3-diol, 2,2-dibromo-2-ethanol, 2-bromo-4'-hydroxyacetophenone, dibromonitrile propionamide and 2-bromo-2-bromomethylglutarnitrile, and examples of natural essential oils include cineol, hinokitiol, menthol, terpineol, borneol, nopol, citral, citronellal, citronellol, geraniol, linalool, dimethyloctanol and thymol.

The multi-molecular host compound refers to a compound forming a crystalline complex (clathrate compound) in the form that two or more host compounds surround one molecule of a guest antimicrobial agent. There are no particular restrictions if a compound has the above properties. Examples include tetrakisphenols, 1,1,6,6-tetraphenyl-2,4-hexadiyn-1,6-diol, 1,6-bis(2-chlorophenyl)1,6-diphenylhexan-2,4-diyn-1,6-diol, 1,1,4,4-tetraphenyl-2-butyn-1,4-diol, 2,5-bis(2,4-dimethylphenyl)hydroquinone, 1,1-bis(2,4-dimethylphenyl)-2-propyn-1-ol, 1,1,2,2-tetraphenylethan-1,2-diol, 1,1-bi-2-naphthol, 9,10-diphenyl-9,10- dihydroxyanthracene, 1,1,6,6-tetra(2,4-dimethylphenyl)-2,4-hexadiyn-1,6-diol, 9,10-bis(4-methylphenyl)-9,10-dihydroxyanthracene, 1,1-bis(4-hydroxyphenyl) cyclohexane, N,N,N',N'-tetrakis(cyclohexyl)-(1,1'-biphenyl)-2,2'-dicarboxyamide, 4,4'-sulfonylbisphenol, 4,4'-butylidenebis(3-methyl-6-tert-butylphenol), 2,2'-methylenebis(4-methyl-6-tert-butylphenol), 4,4'-thiobis(4-chlorophenol), 2,2'-methylenebis(4-chlorophenol), deoxycholic acid, cholic acid, α,α,α',α'-tetraphenyl-1,1'-biphenyl-2,2'-dimethanol, t-butylhydroquinone, 2,5-di-tert-butylhydroquinone, granular corn starch and 1,4-diazabicyclo-(2,2,2)-octane.

Actual examples of the above tetrakisphenols include tetrakis(hydroxyphenyl) alkanes such as 1,1,2,2-tetrakis(4-hydroxyphenyl)ethane, 1,1,2,2-tetrakis(3-fluoro-4-hydroxyphenyl)ethane, 1,1,2,2-tetrakis(3-chloro-4-hydroxyphenyl) ethane, 1,1,2,2-tetrakis(3-methyl-4-hydroxyphenyl)ethane, 1,1,2,2-tetrakis(3-methoxy-4-hydroxyphenyl)ethane, 1,1,2,2-tetrakis(3,5-dimethyl-4-hydroxyphenyl)ethane, 1,1,3,3-tetrakis(4-hydroxyphenyl)propane, 1,1,3,3-tetrakis(3-fluoro-4-hydroxyphenyl)propane, 1,1,3,3-tetrakis(3-chloro-4-hydroxyphenyl)propane, 1,1,3,3-tetrakis(3-methyl-4-hydroxyphenyl)propane, 1,1,3,3-tetrakis(3-methoxy-4-hydroxyphenyl)propane, 1,1,3,3-tetrakis(3,5-dimethyl-4-hydroxyphenyl)propane, 1,1,4,4-tetrakis(4-hydroxyphenyl)butane, 1,1,4,4-tetrakis(3-fluoro-4-hydroxyphenyl)butane, 1,1,4,4-tetrakis(3-chloro-4-hydroxyphenyl)butane, 1,1,4,4-tetrakis(3-methyl-4-hydroxyphenyl)butane, 1,1,4,4-tetrakis(3-methoxy-4-hydroxyphenyl)butane, 1,1,4,4-tetrakis(3,5-dimethyl-4-hydroxyphenyl)butane, 1,1,5,5-tetrakis(4-hydroxyphenyl)pentane, 1,1,5,5-tetrakis(3-fluoro-4-hydroxyphenyl)pentane, 1,1,5,5-tetrakis(3-chloro-4-hydroxyphenyl)pentane, 1,1,5,5-tetrakis(3-methyl-4-hydroxyphenyl)pentane, 1,1,5,5-tetrakis(3-methoxy-4-hydroxyphenyl)pentane and 1,1,5,5-tetrakis(3,5-dimethyl-4-hydroxyphenyl)pentane.

Organic iodine antimicrobial agents having wider antimicrobial spectra than other antimicrobial agents and being safe on human bodies such as those used for commercially available gargles can be advantageously used as microorganism growth retarding substances in the present invention. In this case, the organic iodine antimicrobial agents are preferably solid, although there are no particular restrictions on them. Their examples include 2,3,3-triiodoallyl alcohols, 2,3,3-triiodoallyl ethers, 2,3,3-triiodoallylazoles, 3-iodo-2-propagylbutylcarbamic acid, 4-chlorophenyl(3-iodopropagyl)formal, iodopropagylazoles, diiodo-para-trisulfone, povidone iodine, benzyliodine acetate and para-nitrobenzyliodine acetate. They are used alone or a mixture of two or more.

When using the aforementioned various known germicides, antimicrobial agents, mildew proofing agents or the like as microorganism growth retarding substances, or known slime preventing/removing agents containing them, or the said clathrate compounds or organic iodine antimicrobial agents, they may be mixed with appropriate blending substances and molded to proper sizes by known methods such as pressure molding, heat-melt mix molding or knead-extrusion molding in order to prevent active ingredients from flowing out more than required on contacting drainage and to dissolve the ingredients into the drainage at appropriate rates.

Examples of blending substances for pressure molding include a variety of known excipients, dissolution regulators, binders, glazing agents, surface active agents and corrosion inhibitors.

Examples of the excipients, binders and dissolution regulators include various organic acids such as fumaric acid, benzoic acid, adipic acid, succinic acid, sulfamic acid, boric acid, dl-malic acid, citric acid, ascorbic acid, malonic acid and glycolic acid; inorganic acids, lactic acid, glucose, various starches such as corn starch, crystalline cellulose, powder cellulose, sodium chloride, magnesium sulfate, potassium sulfate, calcium sulfate, calcium hydrogen phosphate, synthetic aluminum silicate, magnesium trisilicate, methyl cellulose, ethyl cellulose, carboxymethyl cellulose, carboxymethyl cellulose sodium, carboxymethyl cellulose calcium, hydroxypropyl cellulose, polyvinyl alcohol, polyvinyl pyrolidone, sodium alginate, gum arabic (powder), sucrose fatty acid esters and $C_{14}$ to $C_{24}$ saturated fatty acids. These excipients, binders and dissolution regulators may be added at a ratio of 1 to 99% by weight to the total solid weight.

Examples of glazing agents include magnesium stearate, calcium stearate, sodium stearate, sodium benzoate, ortho-boric acid, silica, talc and waxes. These glazing agents may be used at a ratio of 0.01 to 1 by weight to the total solid weight.

Examples of surface active agents include alkylalkanolamides, sodium dialkylsulfosuccinates and sodium lauryl sulfate. These surface active agents may be used at a ratio of 0.5 to 10% by weight to the total solid weight.

Examples of corrosion inhibitors include alkylthiourea compounds and triazole compounds. The use of these inhibitors can control the corrosion of metal portions of pipes and others.

Blending substances for heat-melt mix molding or knead-extrusion molding are preferably solids having melting points between 40 and 100° C. Their examples include various water-soluble polymers such as polyoxyethylene and surface active agents such as block polymers of polyoxyethylene and polyoxypropylene, polyoxyethylene alkylphenyl ethers, polyehtylene glycol fatty acid esters, glycerin fatty acid esters and polyoxyethylene alkylethers.

Particularly preferred slime preventing/removing agents are the pressure molded products of antimicrobial agents of non-bleaching powder type with specific base materials. Any antimicrobial agent of non-bleaching powder type can be used in the present invention, if it does not react with acidic substances or the like to generate chlorine gas when used. Their examples include common compounds known as mildew proofing agents or antimicrobial agents and natural essential oils known to have antimicrobial activities.

Actual examples of mildew proofing agents or antimicrobial agents include 5-chloro-2-methyl-4-isothiazolin-3-one, 2-methyl-4-isothiazolin-3-one, 4,5-dichloro-3-n-octyl-isothiazolin-3-one, 1,2-benzisothiazolin-3-one, 2-methoxycarbonylbenzimidazole, 2,3,5,6-tetrachloro-4-methanesulfonylpyridine, 2-thiocyanomethybenzothiazole, 2,2-dithio-bis-(pyridin-1-oxide), 3,3,4,4-tetrahydrothiophene-1,1-dioxide, 4,5-dichloro-1,2-dithiolan-3-one, 5-chloro-4-phenyl-1,2-dithiolan-3-one, N-methylpyrolidone, phenyl-(2-cyano-2-chlorovinyl)sulfone, methylenebisthiocyanate, 2-bromo-2-nitropropane-1,3-diol, 2,2-dibromo-2-ethanol, 2-bromo-4'-hydroxyacetophenone, dibromonitrile propionamide, 2-bromo-2-bromomethylglutarnitrile, sodium percarbonate, potassium persulfate, sodium perborate, ortho-phenylphenol, diphenyl, 2-isopropyl-5-methylphenol, para-chloromethaxylenol, n-butyl para-hydroxybenzoate, ethyl para-hydroxybenzoate, methyl para-hydroxybenzoate, benzalkonium chloride, benzethonium chloride, chlorohexidine hydrochloride, chlorohexidine gluconate, 2-pyridinethiol-1-oxide, zinc salts of 2-pyridinethiol-1-oxide, sodium 2-pyridinethiol-1-oxide, N,N'-hexamethylenebis(4-carbamoyl-1-decylpyridinium bromide) and 4,4'-(tetramethylenediamino)bis(1-decylpyridinium bromide).

Examples of natural essential oils include cineol, hinokitiol, menthol, terpineol, borneol, nopol, citral, citronellal, citronellol, geraniol, linalool, dimethyloctanol and thymol.

Iodine antimicrobial agents are also exemplified as the antimicrobial agents of non-bleaching powder type in the present invention. Of them, solids are particularly preferred. Their examples include 2,3,3-triiodoallyl alcohols, 2,3,3-triiodoallyl ethers, 2,3,3-triiodoallylazoles, 3-iodo-2-propagylbutylcarbamic acid, 4-chlorophenyl(3-iodopropagyl)formal, iodopropagylazoles, diiodo-para-trisulfone, popidone iodine, benzyliodine acetate and para-nitrobenzyliodine acetate.

These antimicrobial agents of non-bleaching powder type may be used alone or a mixture of two or more. Antimicrobial agents of non-bleaching powder type that are made into clathrate compounds with the aforementioned multi-molecular host compounds are also preferably used.

Clathrate compounds are easily prepared by reacting guest antimicrobial agents of non-bleaching powder type with host compounds with stirring for several minutes to several hours at a temperature between ordinary temperature and 100° C. and, if required, in the presence of water or organic solvents.

Base materials used together with antimicrobial agents of non-bleaching powder type in the present invention are selected from calcium hydrogen phosphate dihydrate, tricalcium phosphate anhydride, magnesium hydrogen phosphate tri-hydrate, magnesium hydrogen phosphate octahydrate, lactose, vanillin, calcium citrate tetra-hydrate, calcium sulfate dihydrate, calcium sulfate hemi-hydrate, acetoacetate anilide, acetoacetate-o-toluidide, acetoacetate-p-toluidide, acetoacetate-o-anicidide, sorbitol, alkylsorbitan esters (HLB: 14 or less), nonionic surface active agents such as glycerin monofatty acid esters, and sucrose fatty acid esters (HLB: 14 or less). They may be used alone or a mixture of two or more. It is desirable to decide by taking into consideration effects on tabletability when pressure molding, solubility in water, disintegration and stability of antimicrobial agents.

Preferred base materials are neutral substances that do not increase chlorine gas generation when mixed with commercially available detergents containing hypochlorites. Sorbitol, lactose, acetoacetate-o-toluidide and calcium sulfate hydrates are particularly preferred when clathrate compounds are used as antimicrobial agents of non-bleaching powder type. Furthermore, calcium sulfate hemi-hydrates are preferred, when calcium sulfate is used as a base material, from the viewpoint of easy control of moldability and solubility. Among calcium sulfate hemi-hydrates, the β type prepared by burning at ordinary pressure is more preferred than the α type produced by burning under pressure, in point of hardly causing the deformation of molded products due to absorbing water. When the β-type calcium sulfate hemi-hydrate is used, the combined use with lactose is more preferred in respect to control of the said moldability and solubility.

A mixing ratio between an antimicrobial agent of non-bleaching powder type and a base material in the present invention can change arbitrarily in the range between 1 to 99 parts by weight of an antimicrobial agent of non-bleaching powder type and 99 to 1 part by weight of a base material, as using conditions vary. It is preferably 5 to 20 parts by weight of an antimicrobial agent of non-bleaching powder type and 95 to 80 parts by weight of a base material. When a clathrate compound is used as an antimicrobial agent of non-bleaching powder type, a preferred mixing ratio is 2 to 30 parts by weight of the said clathrate compound and 98 to 70 parts by weight of a base material.

When an antimicrobial agent of non-bleaching powder type and a base material are pressure molded, pressure molding is made easy by adding, as required, a glazing agent such as calcium stearate, magnesium stearate, sodium stearate, sodium benzoate or ortho-boric acid at a ratio of 0.1 to 5% by weight to the total weight of the slime preventing/removing agent, and a binder such as hydroxypropyl cellulose, sodium alginate, polyvinyl alcohol or polyvinyl pyrolidone at a ratio of 1 to 15% by weight to the total weight of the slime preventing/removing agent.

It is possible to add a saturated $C_{14}$ to $C_{24}$ fatty acid, such as stearic acid, in order to improve the stability (swelling and disintegration prevention) of the agent in water as well as giving glazability when molding. Particularly when calcium sulfate is used as a base material, it is preferable to add a saturated $C_{14}$ to $C_{24}$ fatty acid as a dissolution regulator. A saturated $C_{14}$ to $C_{24}$ fatty acid is added at a ratio of 1 to 10% by weight to the total weight of the slime preventing/removing agent. It is possible to add more than 10% by weight. However, the result is a slow dissolving rate. Actual examples of $C_{14}$ to $C_{24}$ saturated fatty acids include stearic acid and lauric acid. Metal salts of the above saturated $C_{14}$ to $C_{24}$ fatty acids used as glazing agents, such as calcium stearate, are not suitable to use as dissolution regulators, because of possible damage to the moldability if they are used at a ratio of more than 1% by weight to the total weight of the slime preventing/removing agent. Further, a corrosion inhibitor, such as alkylthioureas or triazoles, may be added, depending on applications, to control the corrosion of metal portions of pipes and the like. An addition of diatomaceous earth, sulfuric acid clay or the like gives an antistatic effect when molding.

An active ingredient can be spread widely over slime contaminated surfaces by adding various surface active agents. A component giving a bitter taste, if added, may prevent infants from taking in the agent accidentally. It is also possible to control bad smells of kitchen garbage or inlet pipes by adding a deodorant or aromatic.

A solid can take any shape, such as spherical, tablet, cylindrical, rectangular parallelopiped, pyramidal or doughnut-shape, and any size if it can be stored in a container. To use a solid, for example, one cylindrical or doughnut-shaped solid may be used, fitting to the shape of the solid storage of a container. A large number of small granules may be also used. In case a large quantity of small granules are used, it is possible to use granules of the same kind as well as small granular solids of two or more different types, such as chemicals containing different blending ingredients or having different solubilities. Shapes, such as disk, square with corners removed, oval, flat spherical or spherical, are preferably selected because of easy pressure molding and easy installation in narrow places. Small solids of 30 mm or less, preferably 20 mm or less, and particularly preferably 15 mm or less, in the maximum length are effective for spraying a homogeneous solution and adjusting solubility. The present invention covers, for convenience, solids of forms that prevent the active ingredient from flowing out more than required when it contacts with drainage and that let the active ingredient dissolve in the contacted drainage at an appropriate rate, such that a slime preventing/removing agent or the like is stored in a water-permeable bag, tube or the like, made of nonwoven fabric, paper, film or the like, that a slime preventing/removing agent or the like is supported by such a material as sponge or foamed plastic, and that a liquid slime preventing/removing agent or the like is impregnated in a porous mineral and the like.

In the present invention, a container for the storage of solids containing a microorganism growth retarding substance can take any shape, if it has a shape for permitting its installation at the top or upper part of an inlet pipe, has drainage flow-in holes having an opening degree capable of controlling a drainage flow-in amount and provided in the upper surface or the upper side of the container, has solution flow-out holes having an opening degree capable of controlling a flow-out amount of a solid-dissolved solution and provided in the bottom or the lower side, or additionally in the side surface, of the container, and can spread the solid-dissolved solution over slime contaminated wall surfaces. Examples of shapes capable of being installed at the top or the upper part of an inlet pipe include a shape composing a rim formed around the periphery of a ring-shaped container main body, a shape with more than one holder extended from the container main body horizontally, or a shape having more than one holder fixed vertically on the container main body, as well as a filter shape such as a radially cut rubber filter installed at the drain outlet of a kitchen sink or a ring-shaped container capable of setting and fixing to the top or bottom of such a rubber filter with help of the elastic force of an elastic body such as rubber. Containers of this type are used in the condition of being fixed to the filter. It is preferable that such a rubber filter or the like has notches at places corresponding to the drainage flow-in holes or solution flow-out holes provided in a container of this type. In case a container storing a chemical is separated from a filter, such as those mentioned above, it is possible to discard the container only. The present invention also covers integrated types where a container storing solids is attached to an original filter.

To be able to spread a solid-dissolved solution over slime contaminated wall surfaces, it is possible to provide solution flow-out holes in the lower side of the container main body, and also to fix distribution pipes, distribution troughs, pointed distribution fine rods or the like, to the solution flow-out holes or near them.

A solid, if it is of small granules, may be put in from the drainage flow-in holes. When a solid is stored in a container, a container having a structure able to be divided into two and combined with known joint materials, or having an opening for putting in solids and a filter in part of the container, can be used. It is possible to use a container with joint materials integrated to the main body, as mentioned above, to make it possible to install the container at the top or the upper part of an inlet pipe. If there is a stopper or a filter in an inlet pipe or a garbage basket, a container of shape similar to the stopper or filter can be preferably used. Examples of filter shapes include a variety of commercially available filters set in the drain outlets of kitchens, bathrooms and others, such as radially cut rubber filters, plastic filters with garbage flow-in openings at the center of the filter, filters with slit-type garbage collectors that can open and close, and small plate-shaped filters having metal nets or small holes to prevent garbage from coming in and to let only drainage flow in. A container can be simply installed, as it is, if it is a filter to be set in the kitchen sink drain outlet.

Various known materials, such as plastics, rubber and metal, can be used for the containers. A variety of plastics are preferably used from the viewpoint of cost, processing and other conditions. In case a container consists of a filter to be set in a kitchen sink drain outlet, a plastic filter, for example, a colored plastic filter, can be used instead of conventional rubber filters.

Drainage flow-in holes are provided in the upper surface or the upper side of a container and arranged to have an opening degree capable of controlling a drainage flow-in amount, that is, when drainage is in a large quantity, some of the drainage flow into the solid storage through the drainage flow-in holes, but most of it flows out as it is without passing through the drainage flow-in holes. Actual examples include those having one or more adjusted openings in the upper surface or the upper side of a container, and those provided with drainage flow-in holes in the base of a trough adjusted so as to guide only some of the drainage into the drainage flow-in holes. With such drainage flow-in holes provided, a flow-in amount is controlled to prevent a solid-dissolved solution from flowing backward through the drainage flow-in holes, even if water is in a large quantity.

Solution flow-out holes are provided in the bottom or the lower side, or additionally in the side, of the container so as to be able to spread a solid-dissolved solution over slime contaminated wall surfaces. Their actual examples include more than one solution flow-out hole having a controlled opening degree and provided along the top of an inlet or along the upper fringe of a garbage basket, solution flow-out holes provided in the inner side of a filter, such as radially cut rubber filter, to diffuse the solution over the front and back surfaces of the rubber filter, solution flow-out holes having a controlled opening degree and are provided at the base ends of more than one distribution pipe (trough) whose tips can touch the upper part of a drainpipe or garbage basket, and holes provided with pointed distribution fine rods that can touch the upper part of a garbage basket, in the vicinity of the solution flow-out holes, instead of distribution pipes (troughs).

It is particularly preferable to provide solution flow-out holes in the bottom of a container and sides at the peripheral and central sides so that a solution can be diffused over the surrounding area of an inlet pipe, a garbage basket and the front and back surfaces of a rubber filter.

The solution flow-out holes having the controlled opening degree include those having a total opening area so that the maximum amount of water held in a container flows out at a rate of 0.5 to 500 seconds, preferably 2 to 100 seconds, and more preferably 5 to 50 seconds. If solution flow-out holes have a total opening area that the maximum amount of water in a container flows out at faster than 0.5 seconds, the chemical-dissolved solution flows out while a small volume of drainage is still flowing and water used does not finish draining down. As a result, the solution is diluted with water, the chemical staying in the slime contaminated area becomes low in concentration so as to make the slime preventing/removing effect weak, and the chemical is wasted because the chemical-dissolved solution flows down together with the drainage while water is draining. On the other hand, if solution flow-out holes have a total opening area that a flowing-out time exceeds 500 seconds, the flow-out holes become too small in area, and problems, such as the blockage of flow-out holes with garbage or chemical fragments in the draining water, are likely to occur. In the case of less than 2 seconds or exceeding 100 seconds, the tendencies occurring in the above cases of shorter than 0.5 seconds or longer than 500 seconds become very light.

It is possible to prevent and remove slime more efficiently if the total opening area of solution flow-out holes is 0.98 to 0.01, preferably 0.95 to 0.1, of that of drainage flow-in holes. This is because a solid-dissolved solution flows out in a small amount while water is draining even if a drainage amount is large, and a solution of an effective concentration flows out after all water drains down. In case the total opening area of solution flow-out holes exceeds 0.98 of that of drainage flow-in holes, slime preventing/removing effects become insufficient. This is because a small amount of water flows into a container if drainage is flowing down in a short time and it becomes difficult to dissolve a chemical sufficiently and to secure a sufficient amount of the solution to spread over the wall surfaces. If the total opening area of solution flow-out holes is less than 0.01 of that of drainage flow-in holes, the openings of the drainage flow-in holes becomes too wide. As a result, a drainage flow-in rate is too fast and the solution flows backward from the drainage flow-in holes, which may result in wasteful flowing-out of the active ingredient together with draining water or problems such as garbage flowing into the container.

Holes for drainage flowing in or a solution flowing out may take any shape as far as drainage can flow in and a solution can flow out, such as circular, oval, rectangular, star, slit or ring. It is preferable to shape the drainage flow-in holes in slits, numerous small holes, netting, or the like, which are effective to prevent garbage from flowing in. In this case, the slit width or the area of small holes is adjusted in a range that only a small amount of garbage flows in and water flowing in is not blocked due to surface tension. It is possible to cover the openings with a material letting water pass through, such as nonwoven fabric, if it lets drainage flow in. In this case, the total opening area of drainage flow-in holes is considered to be an opening area for an equivalent amount of water flowing through.

Solution flow-out holes are preferably of a slit shape cut from the bottom to the lower side of a container, for the prevention of blockage with flowing-in garbage and the like and advantages in molding. This kind of shape prevents the solution flow-out holes from being completely blocked even if garbage and the like accumulate in the bottom and a chemical from dissolving extremely quickly due to water staying in the container all the time.

If drainage flow-in holes are circular or square, though provided in the upper surface or the upper side of a container, they should be 4 mm or more in diameter or width in order to overcome the water surface tension for guiding drainage into the container smoothly. If holes of this size are made in a container, however, solid garbage, such as food scraps, flows into the container together with draining water in the case of kitchen drain outlets. This results in contaminating the inside of the container, preventing contact between a solid chemical and water, or blocking the drain flow-out holes. Therefore the drainage flow-in holes of the containers of the present invention have a structure to control garbage flowing in. The structures to control garbage flowing in have (1) a shape allowing to guide drainage into the container smoothly and to prevent garbage from flowing into the container, (2) flow-in holes composing hydrophilic nonwoven fabric, and (3) netting flow-in holes. One of these or a combination of these can control garbage flowing into the container.

The shape which guides draining water into the container smoothly and prevents garbage from flowing into the container refers to slit-shaped drainage holes. It is characterized in that drainage flow-in holes are provided at least in the upper surface of the container, and have more than one drainage flow-in slit consisting of one or more slits along the direction to the center of the inlet pipe at appropriate intervals. The slits are 0.5 to 4 mm, further 0.5 to 3 mm, and particularly 1 to 2 mm, wide. Slits of 0.5 mm or wider can let water flow into the container, as the balance of water surface tension is broken, differing from circular holes. The flowing in of garbage can be prevented as much as possible if the slits are 4 mm or narrower, preferably 3 mm or narrower.

If slits are provided along the direction towards the center of the inlet pipe from the periphery where drainage flows into the inlet pipe, even narrow slits can let drainage flow into the container. It is preferable to extend the slits in the upper surface to the side end of the central side of the upper surface of the container and further to provide them continuously to the upper side of the central side. The length of the slits is longer than the width, and is arbitrarily selected. It is preferable to be 2 mm or longer, preferably 5 mm or longer, in the total length of the upper and side portions. Slits may be further extended to the side bottom or to the bottom of the container, being used also as solution flow-out holes.

Materials used for containers with flow-in holes can be made hydrophilic by using hydrophilic plastic materials for the containers, using materials with hydrophilic surface active agents kneaded into container plastics, or applying hydrophilic coating agents or paints onto the surfaces of the containers. Then, the influence of water surface tension is made small. It is therefore possible to let water flow from the drainage flow-in holes of the container into the inside of the container more smoothly and to prevent oils contained in drainage from attaching to the container as well.

It is possible to make drainage flow-in holes of the container that, if composed of hydrophilic nonwoven fabric, let only water infiltrate into the fabric and flow into the container to dissolve a chemical without garbage flowing into it. To do so, the size of the flow-in holes can be arbitrarily chosen in consideration of the infiltration through the nonwoven fabric.

When the flow-in holes of the container have a netting structure, it is possible to let only water flow into the container and dissolve a chemical without garbage flowing into it. To do so, the sizes of the flow-in holes and the netting meshes may be arbitrarily set in consideration of the permeability.

In the present invention, a slime contaminated wall surface refers to an extent having an area, such as plane or curved surface, on which slime is generated, such as the inner wall surface of drainpipes of kitchen sinks, bathrooms and toilet floors, the front and back surfaces of rubber filters at the drain outlets of kitchen sinks, and sides and bottom of garbage baskets installed under the filters or placed in kitchen sinks.

When a small slime preventing/removing agent of the present invention composing tablets of 30 mm or less, preferably 20 mm or less, and more preferably 15 mm or less, in the maximum length is used, a solution can be spread over the slime contaminated surfaces, using a container of the present invention. If slime surfaces are not those of inlet pipes but those of triangular baskets (garbage baskets which are placed in kitchen sinks) or local areas, it is possible to prevent and remove slime with small tablets that are placed in a container composing a bag made of nonwoven fabric, plastic film with fine holes, or the like, and are set at the target place to remove slime by various known fixing means, such as threads, strings, metal lines, plastic stoppers or adhesive tapes.

In case the above small tablets are used, it is possible to attach a flexible tape-shaped material carrying the said preventing/removing agent, to the upper part of slime contaminated wall surfaces and to spread the agent-dissolved solution over the wall surfaces.

A flexible tape-shaped material of the present invention can be any material if it can carry a slim preventing/removing agent containing a microorganism growth retarding substance and spread the solution of the agent over slime contaminated wall surfaces, when adhered, for example, to the upper part of the wall surface of a garbage basket in the sink.

A material for the flexible tape-shaped material can be any material, if it is flexible and at least one side lets water pass through or is water-permeable. Examples of materials having ability to let water pass through or being water-permeable include sponge, foamed plastics, nonwoven fabric, paper and water-permeable film, or combinations of these. A transparent, water-permeable or non-permeable, material, such as a transparent plastic, can be used at least on one side so that the remaining amount of the chemical can be checked visually.

A flexible tape-shaped material can take any structure as far as it can support a slime preventing/removing agent of shape or form, such as powder, fine granule, granule, sphere, tablet, gel or liquid, and the supported agent is dissolved by drainage. For example, the agent-dissolved solution can flow out, when the material is attached to such a place as the upper part of the wall surface of a garbage basket. It is exemplified that a slime preventing removing agent of tablet or another form is put between tape-shaped nonwoven fabrics, papers, water-permeable films or the like, a slime preventing/removing agent of granular or another shape is stored in a bag made of nonwoven fabric, paper, water-permeable film or the like, completely or partly, and a liquid slime preventing/removing agent is impregnated in such a material as sponge or foamed plastic.

Any means is applicable to attach a flexible tape-shaped material to the upper part of the slime contaminated wall surface, as far as it can retain the material at the upper part of the slime contaminated wall surface, such as the upper part of the wall surface of a garbage basket placed in a kitchen sink. The means is roughly grouped into two: to attach to the upper part or the like of the outer wall surface of a garbage basket and to attach to the upper part or the like of the inner wall surface of a garbage basket. The latter means is exemplified by the use of a flexible tape-shaped material itself or a flexible material having restitutive force in part of it in order to press the material to attach to the upper part of the inner wall, more than one protrusion fixed to the surface of a flexible tape-shaped material in order to push them into the meshes of a garbage basket for fixing the material to the upper part of the inner wall, and a proper number of inverted L-shaped brackets installed along the upper edge of a flexible tape-shaped material for hooking up on the edge of the garbage basket.

The means to attach on the upper part of the outer wall surface of a garbage basket is further divided roughly into that integrated with flexible tape-shaped materials and that not integrated. Examples of the latter include a fixing material having pins at the both ends, preferably consisting of a fixing material with pins at the two ends of an elastic body and a flexible tape-shaped material having pin holes at the two longitudinal ends. The pins at the ends of the fixing material are pushed into the pin holes at the longitudinal ends of a flexible tape-shaped material. The ends of the two materials are put together so as to be able to attach the flexible tape-shaped material at the upper part of the outer wall surface of a garbage basket. Fixing materials of this type are advantageously used in particular when applied to portions of slime to be removed with different peripheral lengths, such as garbage baskets of various outer sizes placed in kitchen sinks. In other words, a flexible tape-shaped material provided in a spiral form and with pin holes made at proper intervals in the longitudinal direction is cut to fit the peripheral length of the garbage basket and the pins at the ends of the said fixing material are pushed into the pin holes located near the cut ends for connecting both ends. Thus the flexible tape-shaped material can be attached and retained at the upper part of the wall surface of a garbage basket.

Examples of those integrated with flexible tape-shaped materials include fixing means provided at least at the two longitudinal ends of a flexible tape-shaped material, such as a material with pins at one longitudinal end and pin holes at the other end for connecting the two longitudinal ends of the tape-shaped material, a material with an adhesive tape on each longitudinal end, a material with a Magic Tape (Trade name) on each longitudinal end, and a material with engaging parts fixed at the two longitudinal ends, such as an engaging convexity having a T shape and provided at one longitudinal end and an engaging dent having a T shape and provided at the other longitudinal end. A flexible tape-shaped material with Magic Tape (Trade name) provided on each surface of the two longitudinal ends can apply on slime removing portions of different peripheral lengths, such as garbage baskets of various outer sizes placed in kitchen sinks. In this case, the flexible tape-shaped material is cut to a required length and the cut ends are pressed to adhere so that the flexible tape-shaped material can be held at the upper part of garbage baskets of various sizes.

When inlet pipes are those of bathrooms, a container storing solids may be preferably used if it is provided with drainage guiding openings to make water contact the solids, flow-out openings for solutions of chemicals dissolved in drainage and fixings capable of fixing the storing container at least to one of the front and back sides of a drain grill at the bathroom drain outlet, and has a flat portion capable of adhering to the drain grill at the drain outlets, particularly if drainage guiding openings are provided at least in the side walls of the storing container.

The slime removers of the present invention, particularly those applied to rubber filters at the drain outlets of kitchen sinks or to garbage baskets set under them, are concretely described. The technical scope of the present invention is not, however, limited to these descriptions.

FIG. 1 shows a Slime Remover 1 of the present invention, that consists of ring-shaped Container Main Body 2 fitted to a shape of an inlet pipe or a garbage basket and four pieces of Holder 3 to sit Container Main Body 2 at the upper part of the inlet pipe or basket. It has two or more rectangular Drainage Flow-in Holes 4 in the mildly angled upper surface of Container Main Body 2, and two or more circular Solution Flow-out Holes 5 in the lower side of Container Main Body 2. Container Main Body 2, though not illustrated, is constructed so that the upper and lower main bodies can be vertically separated into two. The space between the upper and lower main bodies forms a storage capable of storing a solid containing a microorganism growth retarding substance (hereinafter referred to as "chemical").

FIG. 2 is a vertical cross-section when the above Slime Remover 1 with more than one small spherical piece of Chemical 6 is applied to Garbage Basket 9 under Rubber Filter 8 at Kitchen Sink Drain Outlet 7. Rubber Filter 8 usually has drainage flow-out holes, such as shown in FIG. 3. When drainage is in a large volume, most of it flows out from Center 10 and drains down as it is. Some of it flow down through Circular Holes 11 provided in the peripheral portion. Some of the flowing drainage reaches the chemical storage through Drainage Flow-in Holes 4 and dissolves Chemical 6. The chemical-dissolved solution flows out from Solution Flow-out Holes 5 about when no more water drains down, flows down along the wall of Garbage Basket 9, and diffuses over the bottom surface on reaching the bottom so as to efficiently remove slime. In the case of insufficient slime removal on the bottom surface of Garbage Basket 9, it is possible to make a small number of solution flow-out holes in the bottom of the inner side of Container Main Body 2.

FIG. 4 shows a Slime Remover 1 of the same type as that shown in FIG. 1. This Slime Remover 1 has Rim 12 to sit Container Main Body 2 at the upper part of an inlet pipe or garbage basket. Two or more Drainage Flow-in Holes 4 are circular in shape. More than one Solution Flow-out Hole 5 have a rectangular shape. A chemical to be stored can be of small spherical shape. Beads can also be used so as not to move around in the storage. In addition, it may be a ring-shaped one fitted to the shape of the storage container.

A Slime Remover 1 of the present invention, shown in FIG. 5, is composed of Container Main Body 2 with Chemical Storage 13 provided in part of the ring fitted to the shape of an inlet pipe or garbage basket and four pieces of Holder 3 to sit Container Main body 2 at the upper part of the inlet pipe or garbage basket. Drainage Flow-in Hole 4 consisting of more than one slit is provided in the upper surface of Container Main Body 2. Two or more circular Solution Flow-out Holes 5 are in the lower side of Container Main Body 2. The slit portion of Drainage Flow-in Hole 4, though not illustrated, is designed to be a lid for storing a chemical. From this hole, 1 to 3 pieces of relatively big Chemical 6, for example, cylindrical, can be inserted. FIG. 6 shows a vertical cross-section when this Slime Remover 1 is applied to Garbage Basket 9 under Rubber Filter 8 at Kitchen Sink Drain Outlet 7.

FIGS. 7 and 8 show Slime Removers 1 of the present invention that can apply to inlet pipes and garbage baskets of various diameters. These Slime Removers 1 are composed of Container Main Body 2 of shape of ring or the like that is smaller than the diameters of inlet pipes or garbage baskets, and, for example, 4 pieces of Holder Trough 14 that sit Container Main Body 2 at the upper part of an inlet pipe or garbage basket and work as drainage guiding troughs as well, and two or more Distribution Pipes 15 (FIG. 7) or Distribution Troughs 16 (FIG. 8) extending from two or more Solution Flow-out Holes 5 provided in the lower side of Container Main Body 2 and whose tips can touch the upper part of the drainpipe or garbage basket. There are two or more rectangular Drainage Flow-in Holes 4 in the bottom of the circumferential groove of the upper surface of Container Main Body 2.

The above Holder Troughs 14 may have a U shape only in the upper surface for easy drainage guiding, as shown in FIG. 7, or are flat plates as shown in FIG. 8. For the convenience of applying to inlet pipes and garbage baskets of various diameters, it is preferable to make Holder Troughs 14 longer beforehand and to cut them to fit to the diameters. The said Distribution Pipes 15 and Troughs 16 are favorably made of flexible materials. Distribution Pipes 15 may be of bugle shape with the tip crushed or of a circular tube shape, as shown in FIG. 7. FIG. 9 shows a vertical cross-section of the key area, when this Slime Remover 1 is applied to Garbage Basket 9 under Rubber Filter 8 at Kitchen Sink Drain Outlet 7. Distribution Pipes 15 and Troughs 16 are used in a condition that their tips are located lower than the base, as shown in FIG. 9.

Furthermore, it is possible to provide protrusions at the tips of Distribution Pipes 15 and Troughs 16, as shown in FIGS. 10 and 11. With such Protrusions 17, when a slime remover of this type is set in a garbage basket, the container main body is pushed in a place a little below the using position of the slime remover and then moved up to the using position by elastic force or the like of the said Holder Trough 14. Then, Protrusions 17 are held by the meshes of a garbage basket. As a result, the tips of Distribution Pipes 15 or Troughs 16 are set more securely at a lower position than the base. FIG. 12 shows a vertical cross-section of the key area when a Slime Remover 1 having Distribution Pipes 15 or Troughs 16 with Protrusions 17 is applied to Garbage Basket 9 under Rubber Filter 8 at Kitchen Sink Drain Outlet 7.

FIG. 13 shows a Slime Remover 1 of the present invention that has Chemical Storage 13 in the periphery of Rubber Filter 18 at Kitchen Sink Drain Outlet 7. This Slime Remover 1 has more than one rectangular Drainage Flow-in Hole 4 in the peripheral upper surface of Rubber Filter 18 and two or more circular Solution Flow-out Holes 5 in the peripheral bottom of Rubber Filter 18. FIG. 14 shows a vertical cross-section when this Slime Remover 1 with Chemical Storage 13 provided in the periphery of Rubber Filter 18 and containing small granules of Chemical 6 is applied to Kitchen Sink Drain Outlet 7.

In FIG. 15, a Slime Remover 1 of the present invention is shown that has Chemical Storage 13 in the side of the outer periphery of Rubber Filter 18 at Kitchen Sink Drain Outlet 7. This Slime Remover 1 is provided with more than one rectangular Drainage Flow-in Hole 4 in the outer peripheral edge of the upper surface of Rubber Filter 18, and with two or more circular Solution Flow-out Holes 5 in the bottom of the peripheral edge and inner side. FIG. 16 shows a vertical cross-section when this Slime Remover 1, with more than one small granule of Chemical 6 filled in a water-permeable tube and set in the inside of Chemical Storage 13 provided in the outer peripheral side of Rubber Filter 18, is applied to Kitchen Sink Drain Outlet 7. The Slime Remover 1 consisting of this Rubber Filter 18 particularly has more than one circular Solution Flow-out Hole 5 in the inner peripheral side of Rubber Filter 18 so as to be able to prevent slime from generating, for example, on the front and back surfaces of radially cut Rubber Filter 18.

FIG. 17 shows a Slime Remover 1 of the present invention, with ring-shaped Chemical Storage 19 capable of fixing freely in the bottom of Rubber Filter 8 which is fixed to Rubber Filter 8 at Kitchen Sink Drain Outlet 7. The ring-shaped Chemical Storage 19 has more than one circular Drainage Flow-in Hole 4 in the upper lid, and more than one circular Solution Flow-out Hole 5 in the bottom of the storage main body. FIG. 18 shows a vertical cross-section when a Slime Remover 1, with the ring-shaped Chemical Storage 19 containing small granules of Chemical 6 in the storage main body which is set and fixed to the bottom of Rubber Filter 8, is applied to Kitchen Sink Drain Outlet 7.

FIG. 19 shows another form of a slime remover of the present invention, with a ring-shaped chemical storage capable of fixing freely in the bottom of Rubber Filter 8 and fixed to Rubber Filter 8 at the drain outlet of a kitchen sink. Rubber Filter 8 has more than one rectangular Drainage Flow-in Hole 23 in the inner peripheral edge, more than one Solution Flow-out Hole 24 in the inner side, and more than one Holding Tab 25 to engage and fix the chemical storage to the bottom of the peripheral outer edge. The ring-shaped chemical storage is composed of a container lid and Container Main Body 19. The container lid has Drainage Flow-in Slits 4 along the direction to the center of the sink drain outlet (corresponding to the above rectangular Drainage Flow-in Holes 23). Container Main Body 19 is equipped with Drainage Flow-in Slits 4 (corresponding to the above rectangular Drainage Flow-in Holes 23) composing more than one slit aligned to the above Drainage Flow-in Slits 4 and Solution Flow-out Holes/Exhausts 26 (corresponding to the above Solution Flow-out Holes 24) in the inner upper side, more than one circular Solution Flow-out Hole 5 in the bottom, and more than one Locating Socket 27 (corresponding to the above Holding Tab 25) in the bottom of the outer peripheral edge. More than one Solution Flow-out Hole/ Exhaust 26 provided in the inner upper side of the chemical storage let a chemical-dissolved solution touch the front and back surfaces of Rubber Filter 8, and function as exhausts as well so that drainage flows in smoothly. FIG. 20 is a rough vertical cross-section when the above slime remover, with a ring-shaped chemical storage storing small granules of Chemical 6 in the storage main body and engaged and fixed to the inside of the bottom of Rubber Filter 8, is applied to the drain outlet of a kitchen sink.

FIG. 21 shows a slime remover similar to that shown in FIG. 19. FIG. 22 is an enlarged view of part of it. A slime remover of this type has Rubber Filter 8 to which a ring-shaped chemical storage capable of fixing freely in the bottom of Rubber Filter 8 is fixed. Rubber Filter 8 has more than one rectangular Drainage Flow-in Hole in the inner peripheral edge, more than one Solution Flow-out Hole in the inner side, and 3 pieces of Holding Tab 25' to engage and fix the chemical storage in the bottom periphery of the inner side. The ring-shaped chemical storage, of which the lid and main body of the container are firmly fixed together, has drainage flow-in slits composing more than one slit along the direction towards the center of the inlet pipe and locating in places from the upper surface to the upper part of the inner side, at the positions corresponding to the above rectangular drainage flow-in holes. It has also more than one circular Solution Flow-out Hole 5 in the inner side, more than one Solution Flow-out Hole/Exhaust 26 in the outer side, more than one circular Solution Flow-out Hole 5 in the bottom, and more than one Solution Flow-out Hole/Exhaust 26' in the outer side.

FIG. 23 shows a Slime Remover 1 of the present invention with ring-shaped Chemical Storage 19 capable of fixing freely in the inner upper side of Rubber Filter 8 and fixed to Rubber Filter 8 at Kitchen Sink Drain Outlet 7. The ring-shaped Chemical Storage 19 has more than one rectangular Drainage Flow-in Hole 4 in the upper surface of the filter, and more than one circular Solution Flow-out Hole 5 in the bottom of the storage main body. Chemical Storage 19, fixed to the inside of the upper part of Rubber Filter 8, lets a chemical-dissolved solution touch the front and back surfaces of Rubber Filter 8. FIG. 24 is a vertical cross-section when this Slime Remover 1, with ring-shaped Chemical Storage 19 storing small granules of Chemical 6 in the storage main body and engaged and fixed to the inside of the upper part of Rubber Filter 8, is applied to Kitchen Sink Drain Outlet 7.

FIG. 25 shows a Slime Remover 1 of the present invention applicable to inlet pipes and garbage baskets of various diameters. This Slime Remover 1 consists of Container Main Body 2 of a ring shape as big as or smaller than the diameter of an inlet pipe or garbage basket, 4 pieces of Holder Trough 14 that sit Container Main Body 2 at the upper part of the inlet pipe or the basket and work as drainage guiding troughs as well, and more than one Pointed Distribution Fine Rod 20 made of plastic or the like, that are integrated in the vicinity of more than one circular Solution Flow-out Hole 5 in the bottom of Container Main Body 2 and whose tips can touch the upper part of a drainpipe or garbage basket. There are two or more rectangular Drainage Flow-in Holes 4 in the bottom of the circumferential groove of the upper surface of Container Main Body 2. A chemical-dissolved solution from Solution Flow-out Holes 5 can reach the wall surface of the inlet pipe or garbage basket by traveling along Pointed Distribution Fine Rods 20, because of its slow flowing-out speed. Pointed Distribution Fine Rods 20 made of plastics or the like are flexible so as to be able to touch the wall surface, even if Container Main Body 2 is smaller than the diameters of inlet pipes or garbage baskets. Container Main Body 2, though not illustrated, is constructed so that the upper and lower main bodies can be vertically separated into two. The space between the upper and lower main bodies forms Chemical Storage 13 capable of storing Chemical 6. Furthermore, the above Holder Troughs 14 may have a U shape only in the upper surface so that drainage can be easily guided. FIG. 26 shows a vertical cross-section of the key area when this Slim Remover 1 is applied to Garbage Basket 9 under Rubber Filter 8 at Kitchen Sink Drain Outlet 7. As shown in FIG. 26, Pointed Distribution Fine Rods 20 are used in the condition that their tips are located lower than the base.

FIG. 27 shows a Slime Remover 1 of the present invention applicable to inlet pipes and garbage baskets where it is difficult to install Container Main Body 2 on their upper part. This Slime Remover 1 consists of Container Main Body 2 of ring shape or the like, and 3 pieces of inverted L-shaped Brackets 21 vertically fixed on Container Main Body 2 and for fixing Container Main Body 2 to the top of an inlet pipe or a garbage basket. There are two or more rectangular Drainage Flow-in Holes 4 in the mildly angled upper surface of Container Main Body 2 and two or more circular Solution Flow-out Holes 5 in the lower side of Container Main Body 2. FIG. 28 shows a rough vertical cross-section of the key area when this Slime Remover 1 is applied to Garbage Basket 9 under Rubber Filter 8 at Kitchen Sink Drain Outlet 7. This Slime Remover 1 can be easily installed even if there are obstacles at an inlet pipe or at the upper part of a garbage basket, such as Basket Handle 22, while installing the remover. It is also possible to make Container Main Body 2 of Slime Remover 1 a little smaller than the diameter of an inlet pipe or a garbage basket and to provide the above Pointed Distribution Fine Rods 20 made of plastic or the like in the vicinity of Solution Flow-out Holes 5.

LEGENDS

Figure 1:
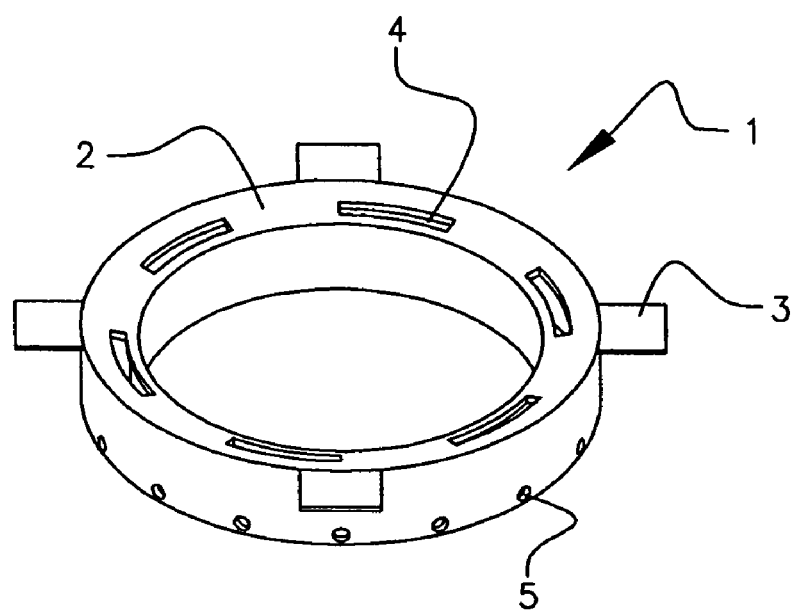
FIG. 1 is a schematic illustration of perspective view of a slime remover of the present invention having plate-type holders.
Figure 2:
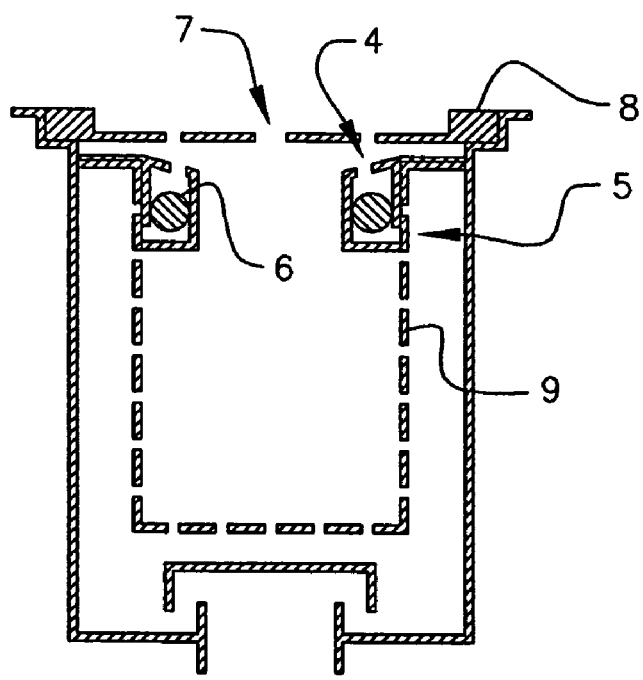
FIG. 2 is a rough vertical cross-section when the slime remover of FIG. 1 is applied to the drain outlet of a kitchen sink.

1. Slime remover
2. Container main body
3. Holder
4. Drainage flow-in hole
5. Solution flow-out hole
6. Chemical
7. Kitchen sink drain outlet
8. Rubber filter
9. Garbage basket
10. Center
11. Circular hole
12. Rim
13. Chemical storage
14. Holder trough
15. Distribution pipe
16. Distribution trough
17. Protrusion
18. Rubber filter (chemical storing type)
19. Chemical storage
20. Pointed distribution fine rod
21. Inverted L-shaped bracket
22. Basket handle
23. Rubber filter drainage flow-in hole
24. Rubber filter solution flow-out hole
25 (25'). Holding tab
26 (26'). Solution flow-out/exhaust
27. Locating socket

BEST FORM TO IMPLEMENT THE INVENTION

The present invention is described concretely in reference to Examples. The present invention is not however limited to these examples.

EXAMPLE 1

Figure 3:
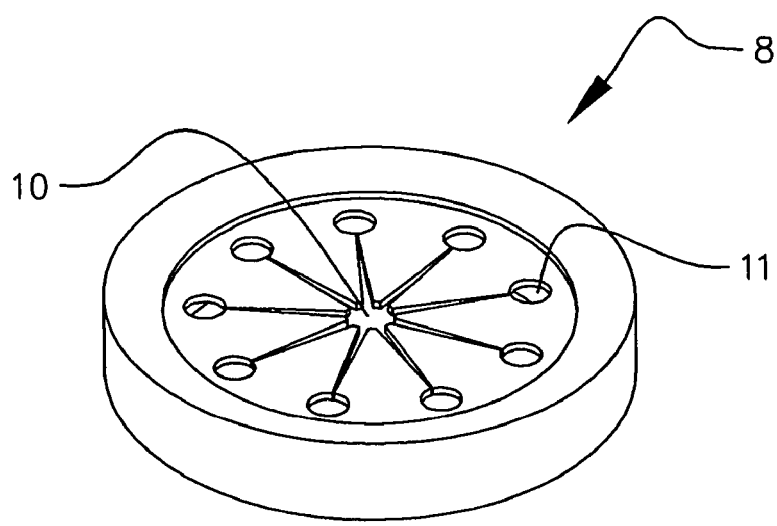
FIG. 3 is a schematic illustration of perspective view of a conventional rubber filter.
Figure 4:
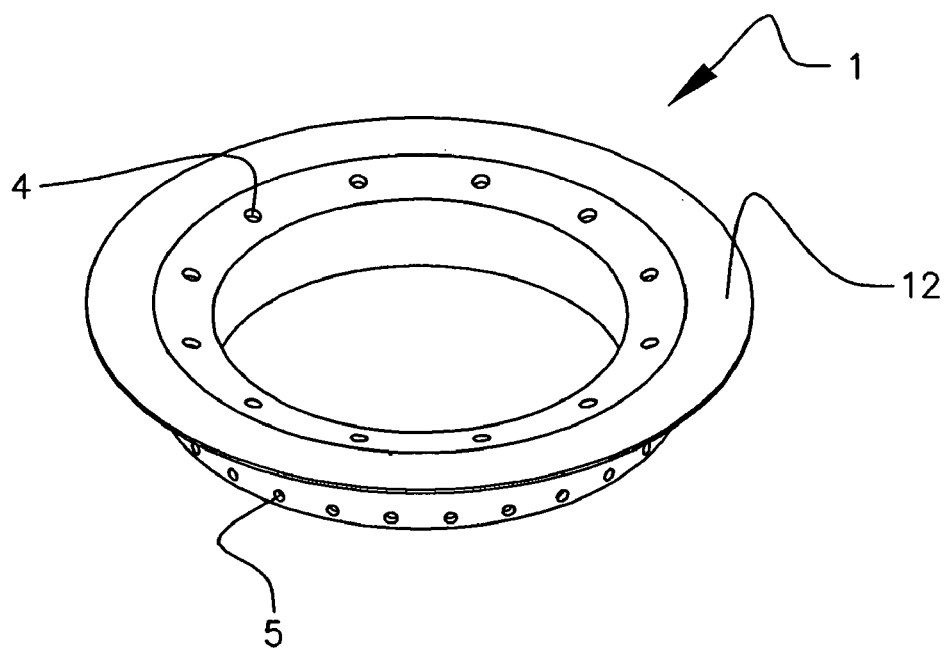
FIG. 4 is a schematic illustration of perspective view of a slime remover of the present invention having a rim.
Figure 5:
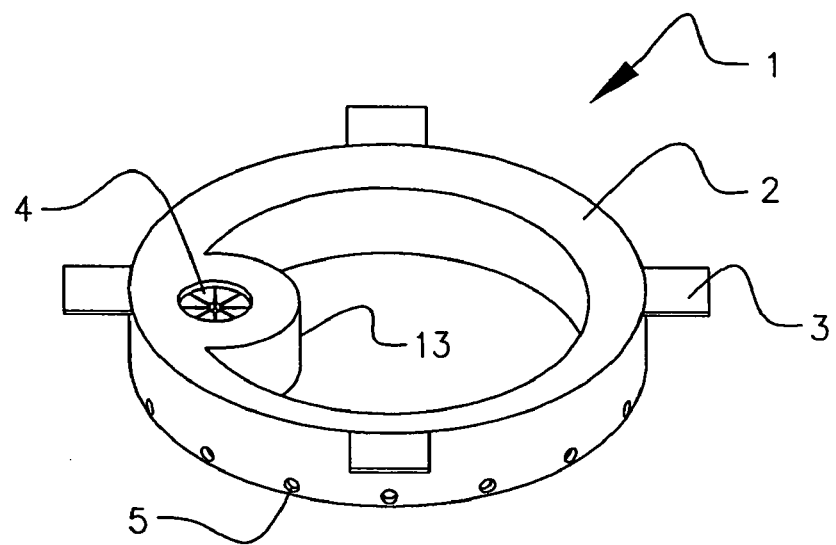
FIG. 5 is a schematic illustration of perspective view of a slime remover of the present invention with a chemical storage provided in part of the ring
Figure 6:
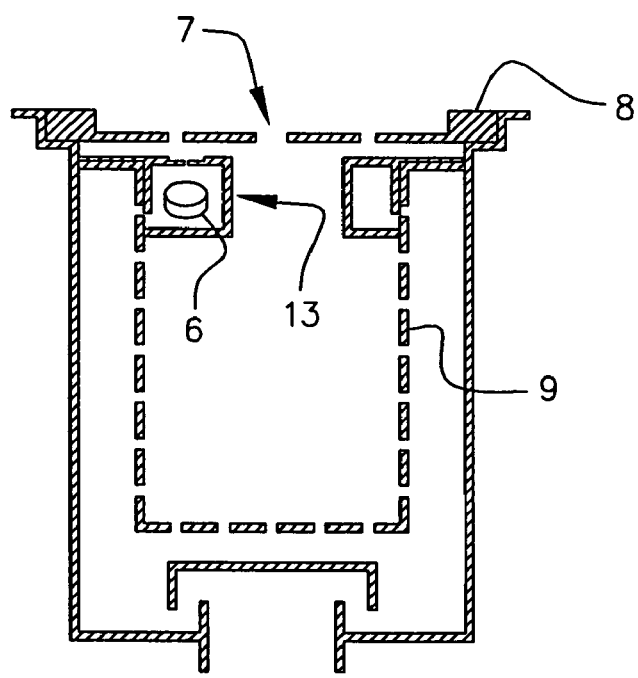
FIG. 6 is a rough vertical cross-section when the slime remover of FIG. 5 is applied to the drain outlet of a kitchen sink.
Figure 7:
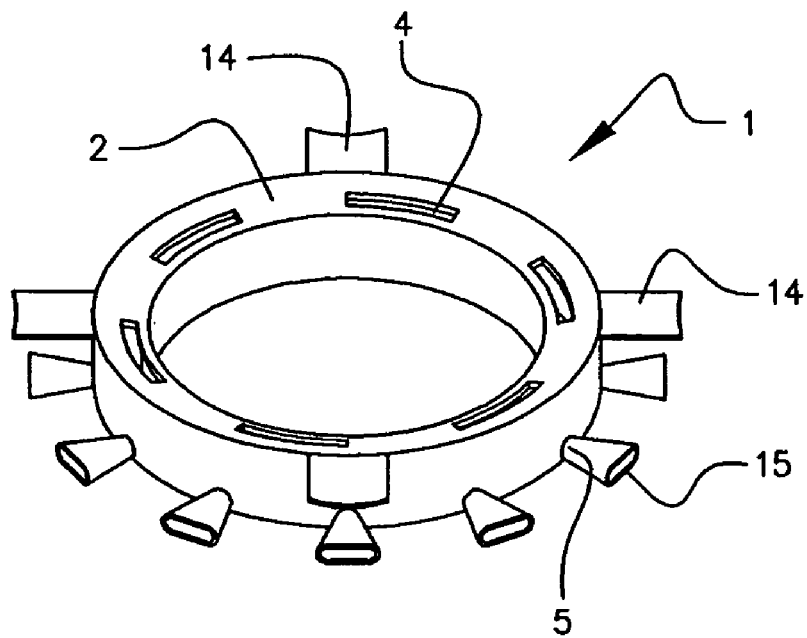
FIG. 7 is a schematic illustration of perspective view of a slime remover of the present invention having distribution pipes.
Figure 8:
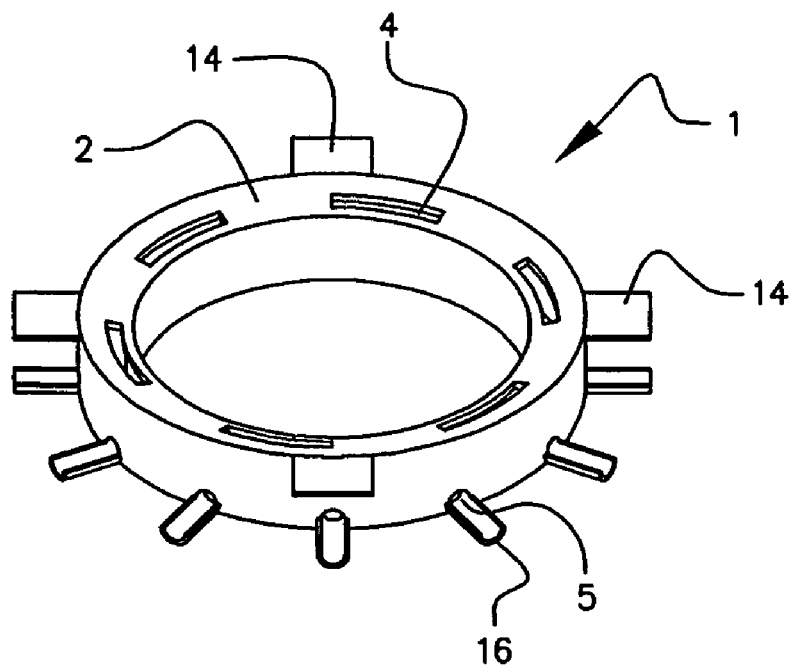
FIG. 8 is a schematic illustration of perspective view of a slime remover of the present invention having distribution troughs.
Figure 9:
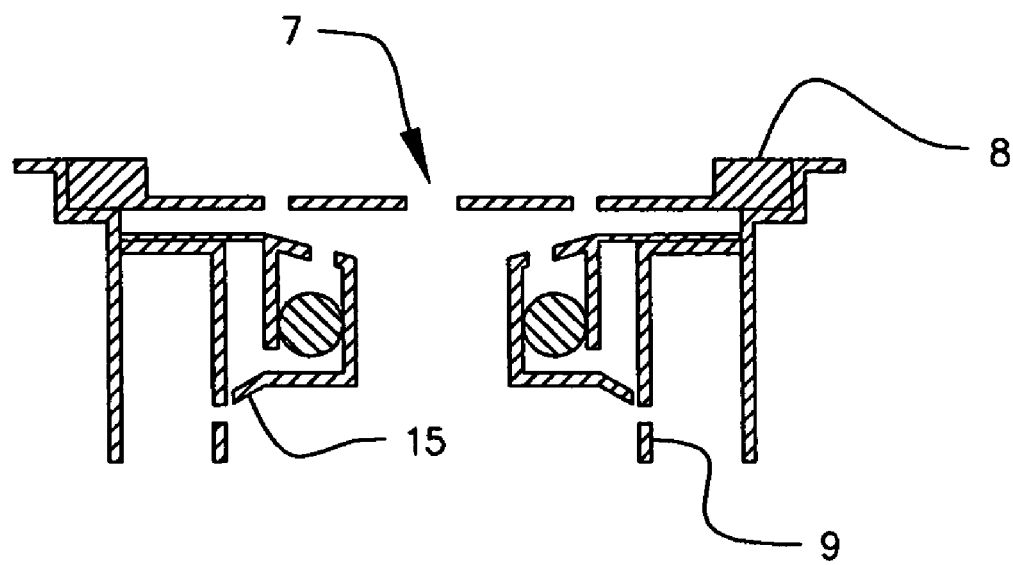
FIG. 9 is a rough vertical cross-section of the key area when the slime remover of FIG. 7 or 8 is applied to the drain outlet of a kitchen sink.
Figure 10:
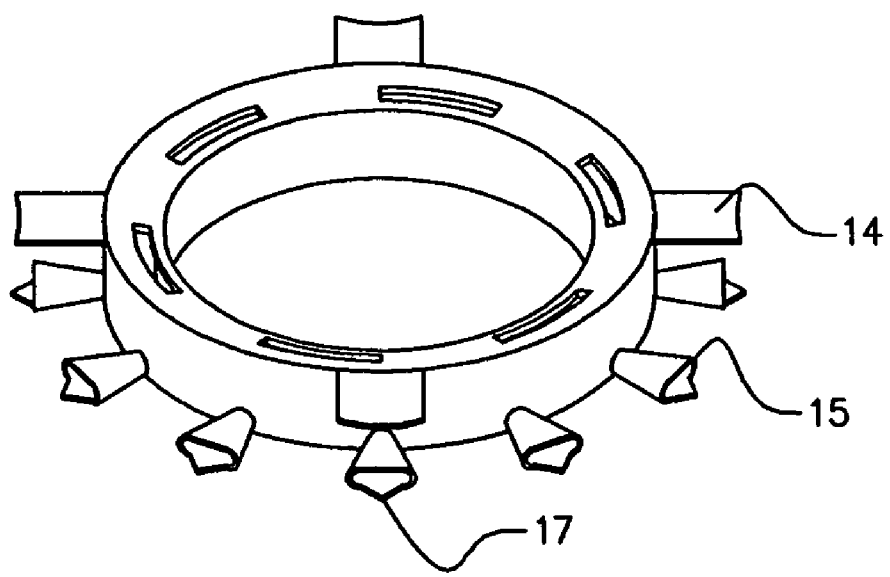
FIG. 10 is a schematic illustration of perspective view of a slime remover of the present invention having distribution pipes with protrusions.
Figure 11:
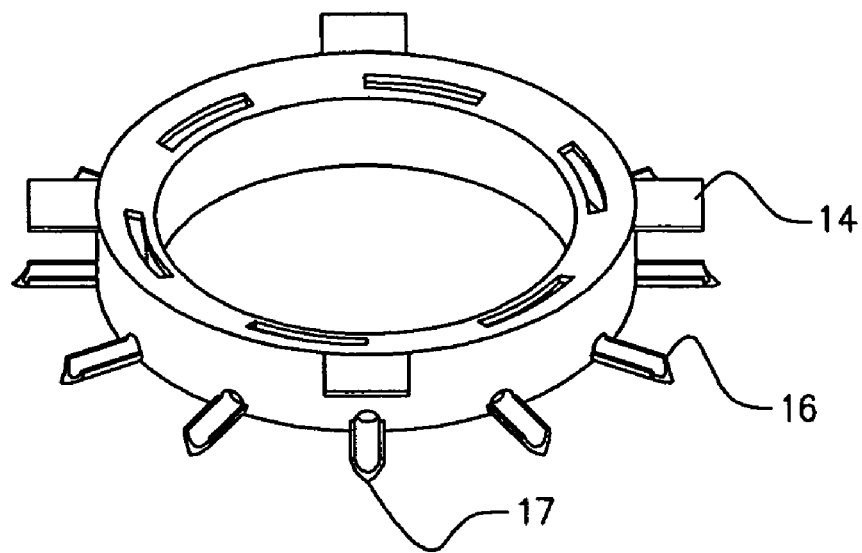
FIG. 11 is a schematic illustration of perspective view of a slime remover of the present invention having distribution troughs with protrusions.
Figure 12:
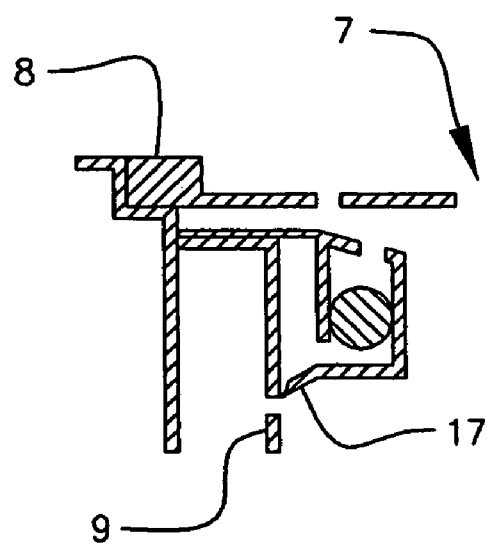
FIG. 12 is a rough vertical cross-section of the key area when the slime remover of FIG. 10 or 11 is applied to the drain outlet of a kitchen sink.
Figure 13:
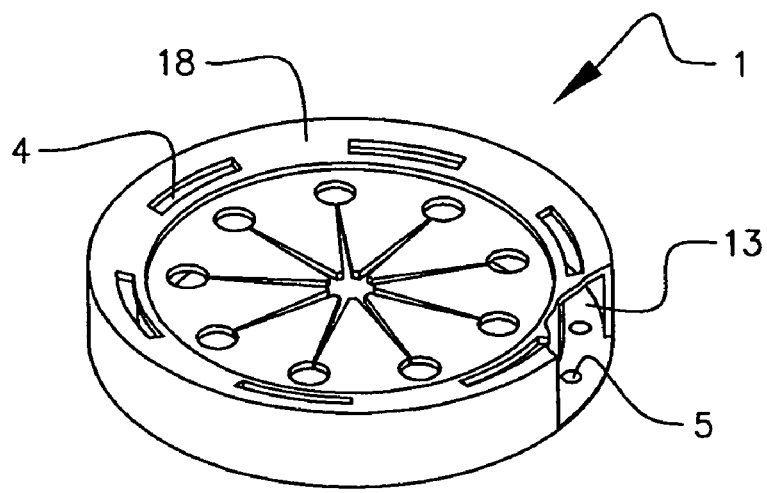
FIG. 13 is a schematic illustration of perspective view of a slime remover of the present invention with a chemical storage provided in the periphery of a rubber filter.
Figure 14:
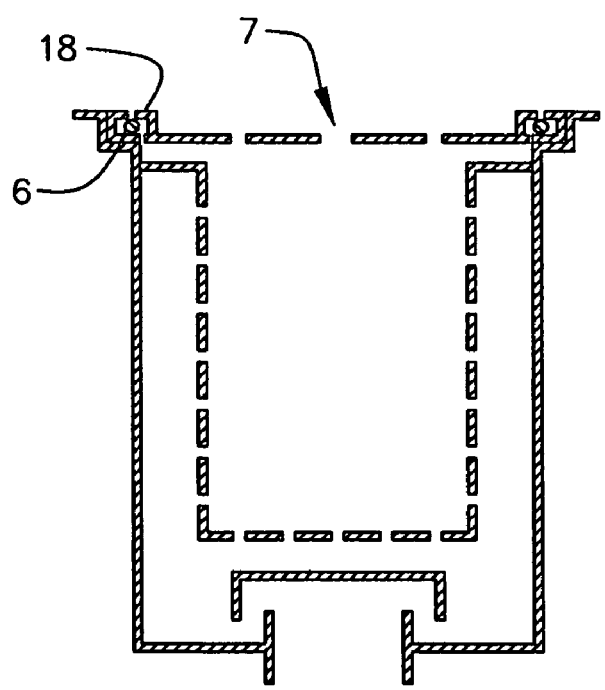
FIG. 14 is a rough vertical cross-section when the slime remover of FIG. 13 is applied to the drain outlet of a kitchen sink.
Figure 15:
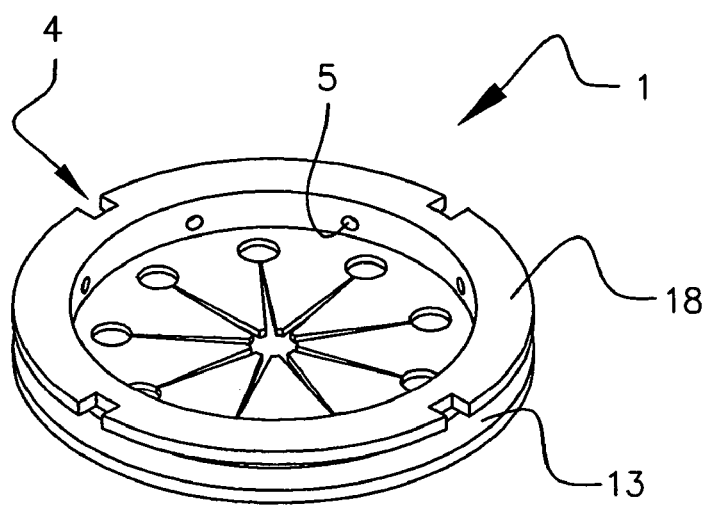
FIG. 15 is a schematic illustration of perspective view of a slime remover of the present invention with a chemical storage provided in the outer peripheral side of a rubber filter.
Figure 16:
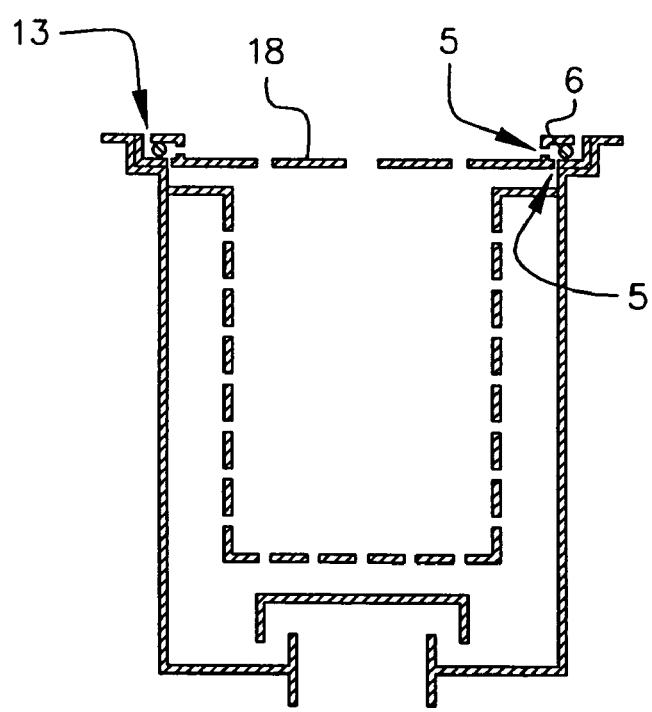
FIG. 16 is a rough vertical cross-section when the slime remover of FIG. 15 is applied to the drain outlet of a kitchen sink.
Figure 17:
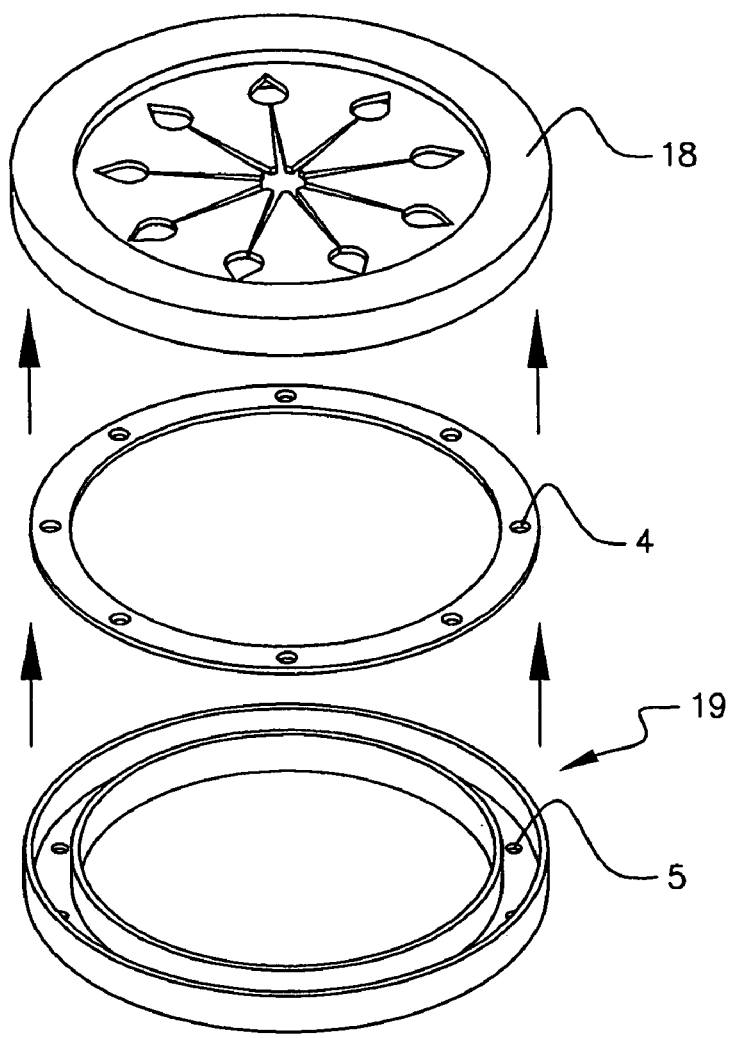
FIG. 17 is a schematic illustration of perspective view of a slime remover of the present invention with a ring-shaped chemical storage freely applicable to the bottom of a rubber filter.
Figure 18:
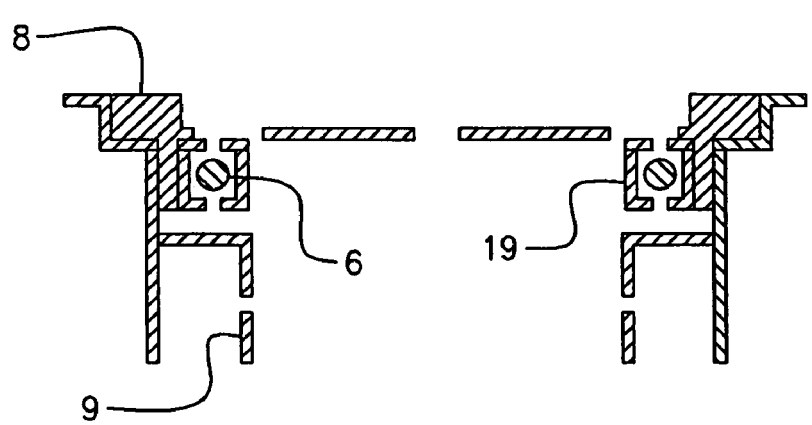
FIG. 18 is a rough vertical cross-section when the slime remover of FIG. 17 is applied to the drain outlet of a kitchen sink.
Figure 19:
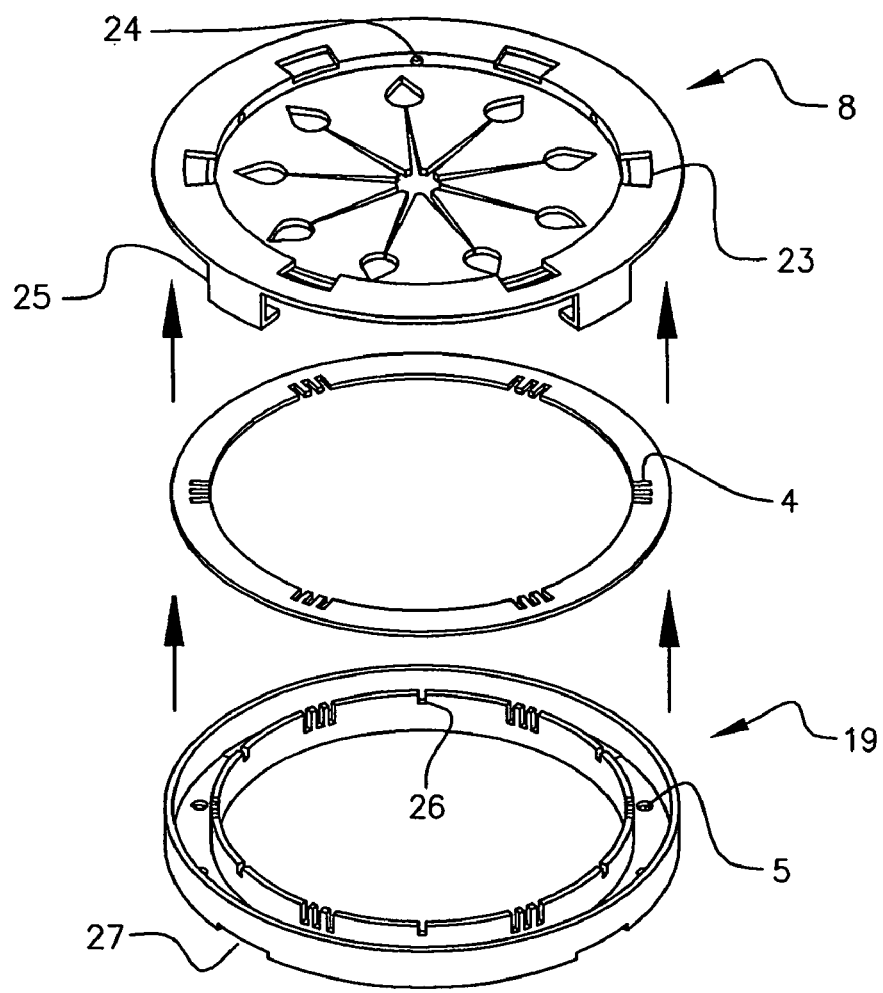
FIG. 19 is a schematic illustration of perspective view of another type of a slime remover of the present invention with a ring-shaped chemical storage freely applicable to the bottom of a rubber filter.
Figure 20:
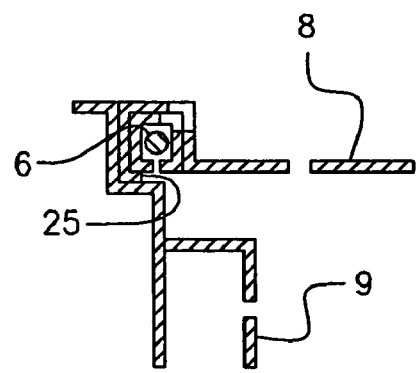
FIG. 20 is a rough vertical cross-section when the slime remover of FIG. 19 is applied to the drain outlet of a kitchen sink.

The dispersibility of a chemical-dissolved solution was tested using a slime remover shown in FIG. 3 (24 drainage flow-in holes of 4 mm in diameter, 12 solution flow-out holes of 2.4 mm×1 mm, and 20 ml of water, the maximum volume the container can hold, flowing out in 20 seconds). A test chemical was prepared in the way that the following ingredients, which are pharmaceutical testing chemicals and are regarded to be stable in terms of color elution, were mixed to make tablets by a manual, oil-pressure tablet machine owned by the investors' institute in order to understand the dispersibility of the chemical solution. A commercially available container for storing a slime remover of chlorine type was hung by a string for the use as a comparative example.

[Chemical Composition]
84.5% of lactose, 10 of hydroxypropyl cellulose, 5% of color index acid blue 9, and 0.5% of magnesium stearate

[Tableting Conditions]
Pressure: 25 kg/cm$^2$ (gauge pressure)
Die and chemical weight: 11 mm in diameter (0.5 g), 30 mm in diameter (12 g)

[Chemicals Used]
Example: 26 disc-type tablets of 11 mm in diameter are stored. (Chemical weight: 0.5 g×26 tablets=13 g)
Comparative Example: 1 disc-type tablet of 30 mm in diameter is stored. (Chemical weight: 12 g)

Test conditions were that a kitchen sink made by Mikado Co., Ltd. with a large sink drain outlet was installed, a transparent PVC plate was applied so as to make drainage observation easy, the slime remover of the present invention or a dissolution container of Comparative Example for DICHLOTOP was set, a rubber filter was placed, and tap water flowed at a rate of about 6 L/min. The dispersibility of the solutions containing color matter was observed in garbage baskets. It was found that, with the slime remover of the present invention, the chemical dispersed all over the garbage basket. With the remover of Comparative Example, the chemical partially touched only the bottom of the dissolution container, because of a string-hanging type.

EXAMPLE 2

Figure 21:
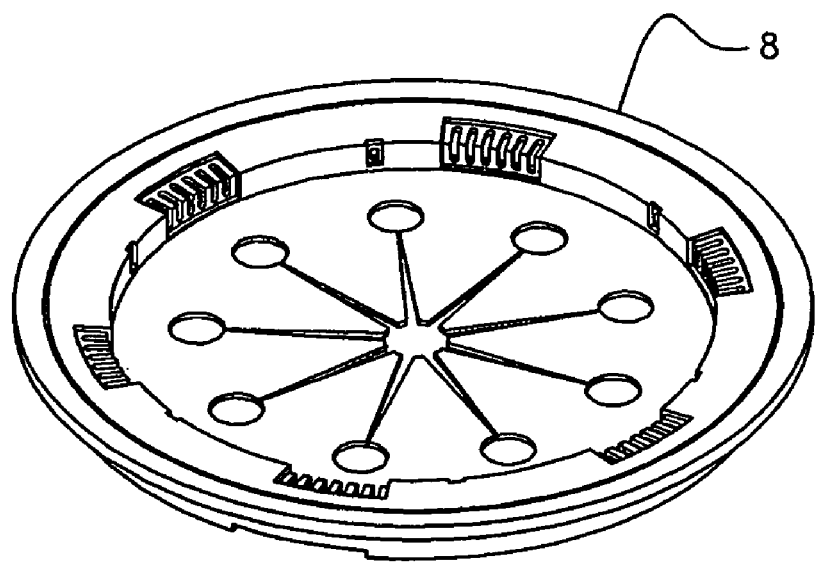
FIG. 21 is a schematic illustration of perspective view of another type of a slime remover of the present invention with a ring-shaped chemical storage freely applicable to the bottom of a rubber filter.
Figure 22:
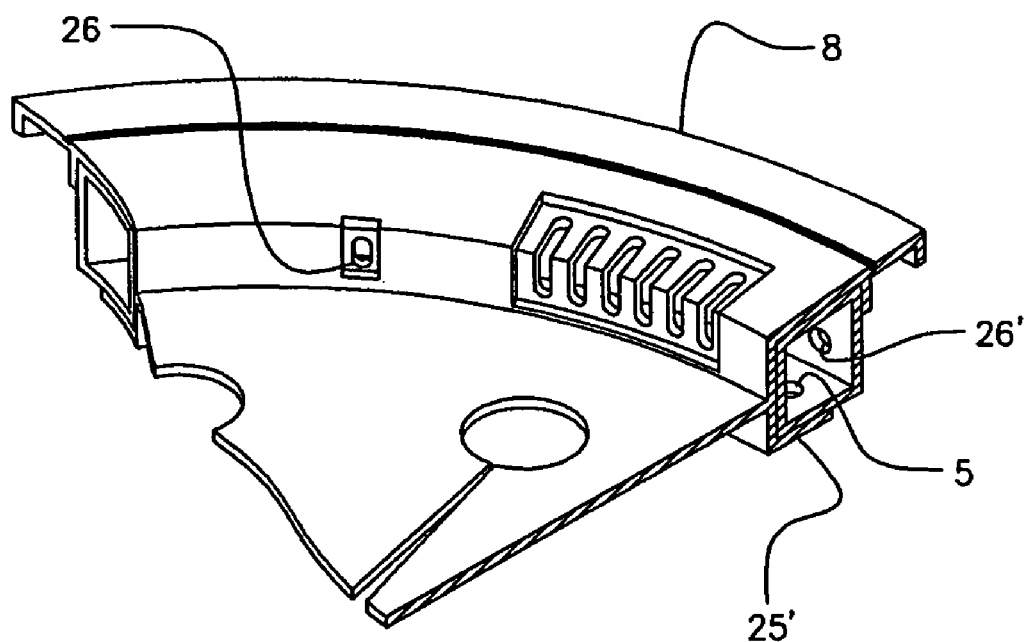
FIG. 22 is an enlarged view of part of the slime remover of FIG. 21.
Figure 23:
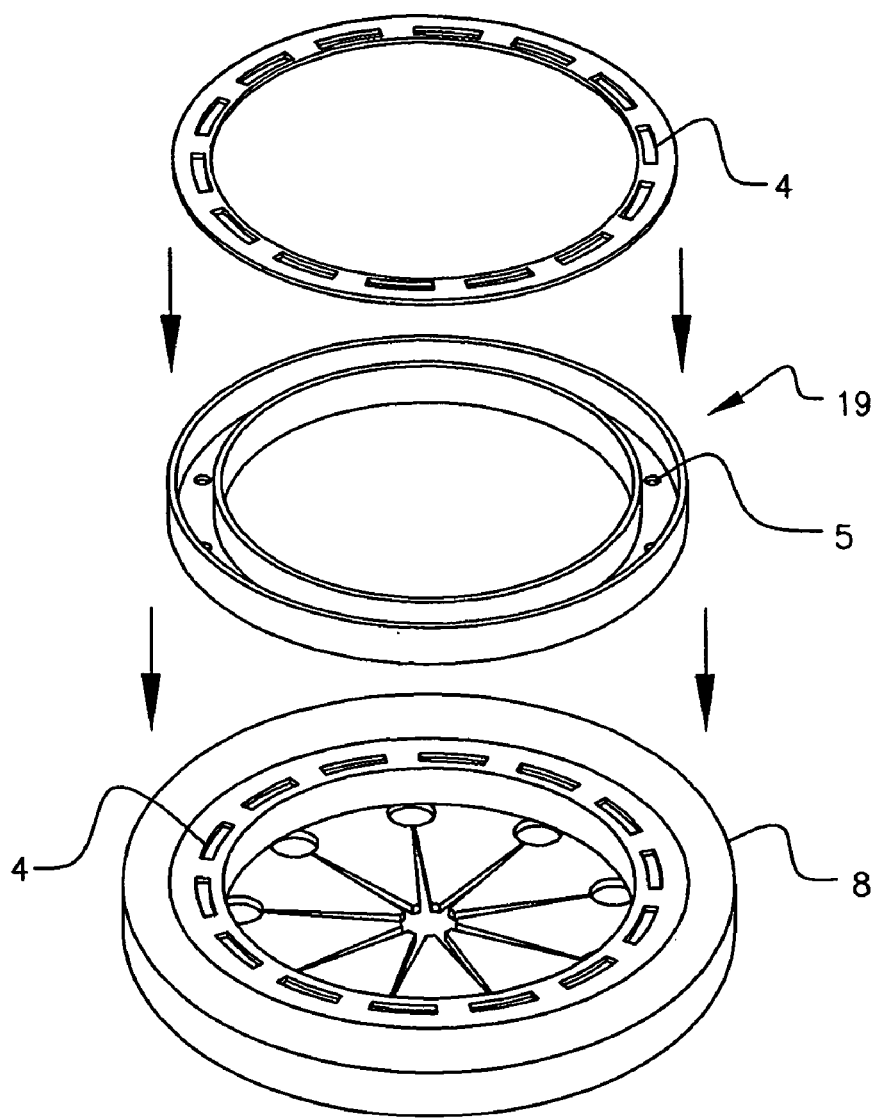
FIG. 23 is a schematic illustration of perspective view of a slime remover of the present invention with a ring-shaped chemical storage freely applicable to the upper part of a rubber filter.
Figure 24:
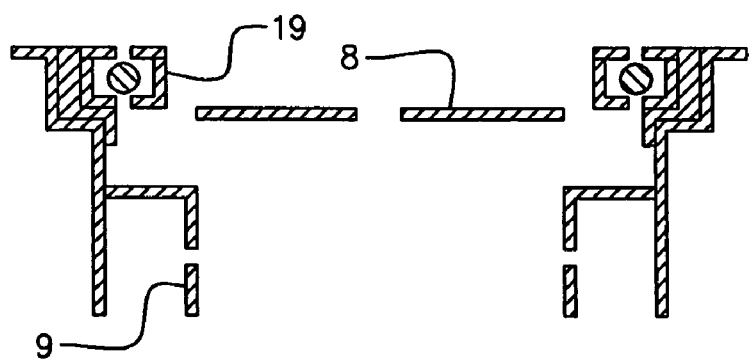
FIG. 24 is a vertical cross-section when the slime remover of FIG. 23 is applied to the drain outlet of a kitchen sink.
Figure 25:
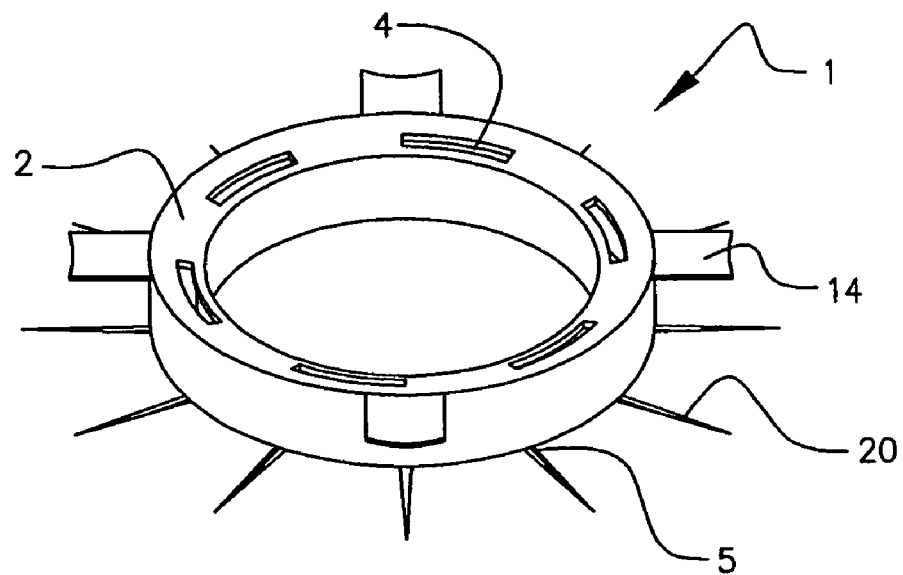
FIG. 25 is a schematic illustration of perspective view of a slime remover of the present invention having pointed distribution fine rods.
Figure 26:
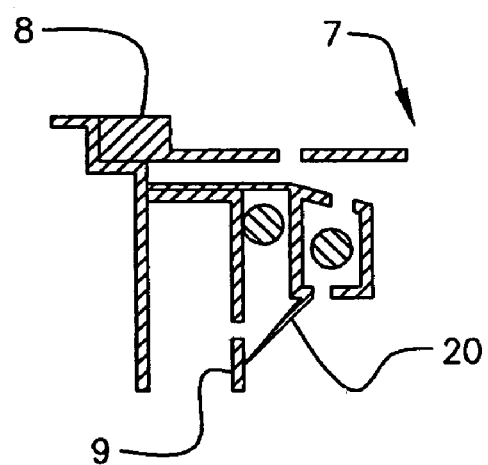
FIG. 26 is a rough vertical cross-section of the key area when the slime remover of FIG. 25 is applied to the drain outlet of a kitchen sink.
Figure 27:
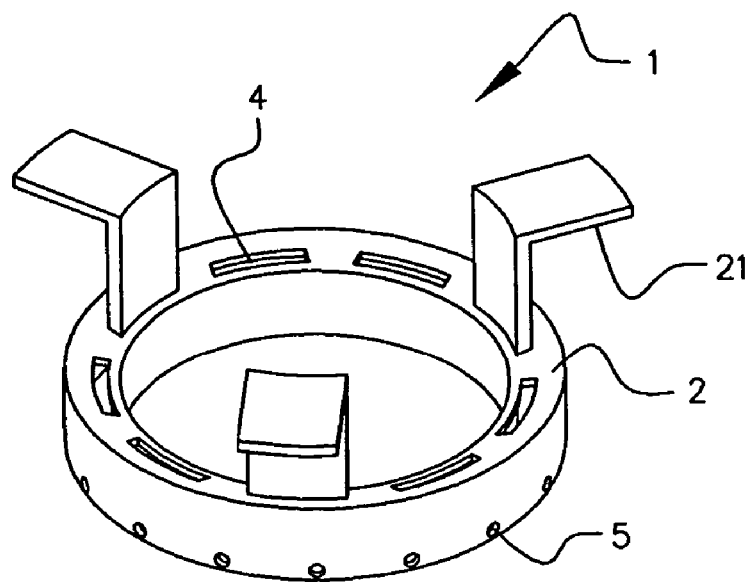
FIG. 27 is a schematic illustration of perspective view of a slime remover of the present invention having inverted L-shaped brackets.
Figure 28:
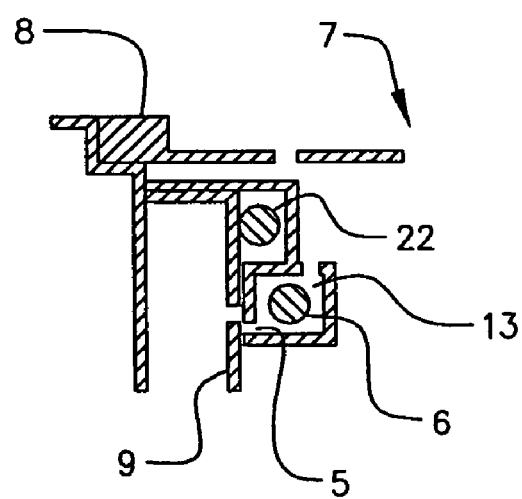
FIG. 28 is a rough vertical cross-section of the key area when the slime remover of FIG. 27 is applied to the drain outlet of a kitchen sink.

Pressure-molded, solid chemicals of 10 mm in diameter were prepared according to the conditions described below. 24 of them were placed in the container of the slime remover shown in FIG. 21 that had a radially cut rubber filter with a chemical storage [container drainage flow-in hole: 6 drainage flow-in slits consisting of 6 slits of 1.5 mm wide and 10 mm long (upper surface 7 mm and upper part of inner side 3 mm), and container solution flow-out hole: 9 holes of 3 mm in diameter in the bottom, 6 holes of 1.5 mm wide×5 mm long in the upper part of the inner side and 6 holes of 2 mm wide×3 mm long in the upper part of the outer side]. The slime remover of the present invention was installed in a household kitchen sink for 2 months for a monitoring test. It was confirmed that no garbage entered into the container, and slime was prevented from generating on the garbage filter, garbage basket, the inner surface of the drainpipe and the like, over the 2 months.

(Chemical Composition and Others)

A mixture of 5 parts by weight of TEP-CMI [a clathrate compound prepared by the reaction between 2 moles of 5-chloro-2-methyl-4-isothiazolin-3-one as a guest antimicrobial agent and 1 mole of 1,1,2,2-tetrakis(4-hydroxyphenyl)ethane as a multi-molecular host compound] and 95 parts by weight of acetoacetate-o-toluidide as a base material was placed in a continuous oil-pressure tablet machine with dies of 10 mm in diameter and tablets of 3 g in weight were made under pressure of 1 t/cm$^2$.

EXAMPLE 3

(Preparation of Samples)

Each of the samples of cylindrically molded products of 10 mm in diameter was prepared by pressure molding from each of the mixtures of blending ratios shown in Table 1. In Table 1, "TEP-CMI" refers to a clathrate compound prepared by the reaction between 2 moles of 5-chloro-2-methyl-4-isothiazolin-3-one as a guest antimicrobial agent and 1 mole of 1,1,2,2-tetrakis(4-hydroxyphenyl)ethane as a multi-molecular host compound; "Bronopol" is an antimicrobial agent, 2-bromo-2-nitropropan-1,3-diol; "TIAA" is 2,3,3-triiodoallyl alcohol, and "HPC" is a binder, hydroxypropyl cellulose.

TABLE 1

| | Sample 1 | Sample 2 | Sample 3 | Sample 4 | Sample 5 | Sample 6 | Sample 7 | Sample 8 | Sample 1* | Sample 2* |
|---|---|---|---|---|---|---|---|---|---|---|
| Benzoic acid | | | | | | | | | 95 | |
| CaSO$_4$·0.5H$_2$O | | | | 60 | 80 | 35 | | | | |
| Acetoacetate-o-toluidide | 95 | | | | | | 55 | | | |
| Acetoacetate-p-toluidide | | | | | | | | 90 | | |
| Acetoacetate-o-anicidide | | 85 | | | | | | | | |
| Sorbitol | | | 98 | | | | | | | |
| Lactose | | | | 22 | | 47 | 35 | | | |
| TEP-CMI | 5 | 5 | 5 | 5 | | 5 | 5 | | 5 | |
| Bronopol | | | | | 10 | | | | | |
| TIAA | | | | | | | | 10 | | |
| Trichloro-isocyanuric acid | | | | | | | | | | 99 |
| Sodium dichloro-isocyanurate | | | | | | | | | | |
| HPC | | 8 | | 10 | 8 | 10 | 5 | | | |
| Lauric acid powder | | 2 | 2 | 3 | 3 | | | | | |
| Stearic acid powder | | | | | | | 3 | | | |
| Calcium stearate | | | | | | | 0.2 | 0.2 | 0.1 | 1 |
| Tabletability | ○ | ○ | ○ | ○ | ○ | ○ | ○ | ○ | ○ | ○ |
| Dissolution rate | 6.1 | 5 | 1 | 11 | 12 | 7 | 5 | 7 | 7 | 8 |
| Bleaching powder smell | ○ | ○ | ○ | ○ | ○ | ○ | ○ | ○ | ○ | x |
| Danger with C1 detergent | ○ | ○ | ○ | ○ | ○ | ○ | ○ | ○ | x | x |
| Amount of slime attached | ○ | ○ | ○ | ○ | Δ | ○ | ○ | Δ | ○ | ○ |

*Samples for comparison (Tableting and Disintegration Tests)

A continuous oil-pressure tablet machine with dies of 10 mm in diameter was installed and tablets were made under heavy pressure of 1 t/cm². A test for "tabletability" was carried out in regard to split, capping, glazability, adhesion and other properties. All the samples were rated as "o" in the tabletability evaluation. None of them were bad in tableting. A tablet of each of the molded samples was placed in a 200-ml plastic cup, and 200 ml of distilled water was added. It was left at room temperature for 24 hours to examine the disintegration of the molded. None of the samples were disintegrated.

(Solubility Tests)

A tablet of a molded product was placed in a commercially available container for storing a slime removing agent. The container with the tablet was set by hanging with a string in water at the depth of 25 to 29 cm in a commercially available pipette cleaner of 18 cm in diameter and 58 cm deep (amount of cleaning water: 14.75L, temperature of cleaning water: 35 to 40° C., cleaning water contacting time: 3 minutes, and cleaning interval: 6.6 minutes/time). It was cleaned continuously and the dissolving rate was measured. The figures in Table 1 show times until the molded products were completely dissolved.

(Performance Tests)

Each sample (molded product) was placed in a commercially available container for storing a slime removing agent. The container was hooked to fix with a string to the drain outlet of a general household kitchen. The odor (bleaching powder smell) and degree of slime attached while using were examined visually a month later. The results are shown in Table 1. As seen from Table 1, none of the samples except that of Comparative Example 2, had bleaching powder smell. As for the amount of slime attached after a month, the evaluation was "Δ" for the sample of Example 5 and a slight amount of slime attached was observed. The evaluations for the others were "o" and no attachment of slime was observed.

(Tests on Chlorine Gas Generation when Mixing with Hypochlorite Detergents)

One gram of a sample was placed in a 100-ml beaker, and 100 ml of distilled water was added. The sample-dissolved solution was measured pH by a pH meter. A pH below 5 was a yardstick to judge that samples would generate chlorine gas when mixing with commercially available hypochlorite detergents. The results are shown in Table 1 as the danger with Cl detergent. As seen from Table 1, the evaluations of the samples of the examples were "o", and there was no fear of generating chlorine gas.

(Disintegration Tests of Clathrate Compounds when they were Used: Elution Tests of Antimicrobial Agents from Clathrate Compounds)

To examine the effect of base materials on the stability of clathrate compounds, disintegration tests on the following clathrate compounds were carried out. One gram of each of various bases shown in Table 2 and 98 g of distilled water were placed in a 200-ml beaker, and stirred with a magnetic stirrer for 3 hours to dissolve up to saturation. Then, 1 g of the said TEP-CMI was added as a clathrate compound, and stirred with a magnetic stirrer for 24 hours. The resulting solution was filtrated through a 0.2µ membrane filter. The amount of the antimicrobial agent eluted from the clathrate compound was measured. Water with no base material added was used as a blank. Table 2 shows the results. In Table 2, "clathrate disintegration (%)" refers to an elution rate of the antimicrobial agent from the clathrate compound. As seen from Table 2, the base materials used in the present invention let the clathrate compound disintegrate approximately as quickly as the blank sample did. Polyethylene oxide used for a comparison caused the disintegration of the clathrate compound at a higher rate. From the viewpoint of the clathrate disintegration rate, the base materials used in the present invention were found to be better.

TABLE 2

| | Base materials of the present invention | | | | | Comparison | |
|---|---|---|---|---|---|---|---|
| | $CaSO_4$ 0.5 $H_2O$ | Acetoacetate-o-toluidide | Acetoacetate-o-anilide | Sorbitol | Lactose | Polyethylene glycol* | Blank |
| Clathrate disintegration (%) | 21 | 21 | 22 | 21 | 18 | 93 | 21 |

APPLICABILITY IN INDUSTRY

The drain slime removers of the present invention can be easily installed in the upper parts of inlet pipes and are excellent in safety and handling. From a container storing a slime preventing/removing agent, an agent-dissolved solution can spread over the wall surface of a drainpipe. Because the opening areas of both drainage flow-in holes and solution flow-out holes are adjusted, only a minimum amount of water required is taken in the inside of the container while drainage is flowing. A chemical-dissolved solution flows out from the container even after water has finished draining. When a conventional basket-type container is used, most of the chemical flows out together with drainage so that the agent can not stay long enough on the slime contaminated portion, having no effect on removing slime. Contrary to this, with the drain slime removers of the present invention, a chemical-dissolved solution, which is not diluted with draining water, contacts slime contaminated portions for a long period of time. Therefore, a small amount of chemical efficiently prevents slime from generating, and an impact on the environment is small even if a chlorine-type chemical is used, thanks to a very small volume of chemical flowing out in drainage. Besides, the active ingredient dissolves at an appropriate rate, so that slime is not only removed but also prevented from generating for a long time, when a remover is installed in a place where slime is generated by metabolites of miscellaneous germs, mildews and the like, such as the drain outlets of kitchen sinks and bathrooms.

The slime preventing/removing agents of the present invention have none of the problems of chlorine smell and corrosion, are excellent in safety and handling, and make it possible to let active ingredients dissolve stably.

What is claimed is:

1. A slime preventing/removing agent for a drain in kitchen sinks and bathrooms comprising a microorganism growth retardant substance, which includes an antimicrobial agent of non-bleaching powder, which is not a clathrate compound, and a multi-molecular host compound, which is pressure molded together with one or more base materials selected from the group consisting of calcium sulfate hemi-hydrate, acetoacetate-o-toluidide, acetoacetate-p-toluidide and acetoacetate-o-anicidide, wherein the multi-molecular host compound is one or more compounds selected from the group consisting of the following compounds:

(1) tetrakisphenols
(2) 1,1,6,6-tetraphenyl-2,4-hexadiyn-1,6-diol,
(3) 1,6-bis(2-chlorophenyl)1,6-diphenylhexan-2,4-diyn-1,6-diol,
(4) 1,1,4,4-tetraphenyl-2-butyn-1,4-diol,
(5) 2,5-bis(2,4-dimethylphenyl)hydroquinone,
(6) 1,1-bis(2,4-dimethylphenyl)-2-propyn-1Ol,
(7) 1,1,2,2-tetraphenylethan-1,2-diol,
(8) 1,1-bi-2-naphthol,
(9) 9,10-diphenyl-9,10-dihydroxyanthracene,
(10) 1,1,6,6-tetra(2,4-dimethylphenyl)-2,4-hexadiyn-1,6-diol,
(11) 9,10-bis(4-methylphenyl)-910-dihydroxyanthracene,
(12) 1,1-bis(4-hyd roxyphenyl)cyclohexane,
(13) N, N, N', N'-tetrakis(cyclohexyl)-(1,1'-biphenyl)-2,2'-dicarboxyamide,
(14) 4,4'-sulfonylbisphenol,
(15) 4,4'-butylidenebis(3-methyl-6-tert-butylphenol),
(16) 2,2'-methylenebis(4-methyl-6-tert-butylphenol),
(17) 4,4'-thiobis(4-chlorophenol),
(18) 2,2'-methylenebis(4-chlorophenol),
(19) deoxycholic acid,
(20) cholic acid,
(21) a,a,a',a'-tetraphenyl-1,1'-biphenyl-2,2'-dimethanol,
(22) t-butylhydroquinone,
(23) 2,5-di-tert-butylhydroquinone,
(24) granular corn starch,
(25) 1,4-diazabicyclo-(2,2 2)-octane.

2. The slime preventing/removing agent according to claim 1, in which the antimicrobial agent of non-bleaching powder is an organic iodine antimicrobial agent.

3. The slime preventing/removing agent according to claim 2, in which the organic iodine antimicrobial agents are 2,3,3-triiodoallyl alcohols, 2,3,3-triiodoallyl ethers, 2,3,3-triiodoallyl azoles, 3-iodo-2-propargyl butyl carbamate, 4-chlorophenyl(3-iodopropargyl)formal, iodopropargyl azoles, diiodo-para-trisulfone, povidon iodine, benzyl iodine acetic ester and paranitro benzyl iodine acetic ester.

4. The slime preventing/removing agent according to claim 1, in which the antimicrobial agents of non-bleaching powder are sodium perborate, benzalkonium chloride, benzethonium chloride, methylenebisthiocyanate, 2-pyridinethiol-1-oxide, zinc 2-pyridinethiol-1-oxide, N,N'-hexamethylenebis(4-carbamoyl-1-decylpyridinium bromide), 4,4'-(tetramethylenediamino)-bis-(1-decylpyridinium bromide) and 2-bromo-2-nitropropane-1,3-diol.

5. The slime preventing/removing agent according to claim 1, in which the antimicrobial agents of non-bleaching powder are 1,2-benzisothiazoline-3-one, 2-methoxycarbonylbenzimidazole, 2,3,5,6-tetrachloro-4-methanesulfonylpyridine, 2,2-dithio-bis-(pyridine-1-oxide), 3,3,4,4-tetrahydrothiophene-1,1-dioxide, 4,5-dichloro-1-,2-dithiolane-3-one, 5-chloro-4-phenyl-1,2-dithiolane-3-one and phenyl-(2-cyano-2-chlorovinyl)sulfone.

6. The slime preventing/removing agent according to claim 1, in which calcium sulfate hemi-hydrate is β-type calcium sulfate hemi-hydrate.

7. The slime preventing/removing agent according to claim 1, in which the slime preventing/removing agent further comprises a $C_{14}$ to $C_{24}$ saturated fatty acid as a dissolution regulator, said $C_{14}$ to $C_{24}$ saturated fatty acid being one of a stearic acid and a lauric acid.

8. The slime preventing/removing agent according to claim 1, in which the molded product is a tablet and the maximum length of the tablet is 15 mm or shorter.

9. A slime removing method comprising:

using a nonwoven fabric bag or a holed plastic film bag, that contains the slime preventing/removing agent according to any one of claims 1 to 8, or using a flexible tape-shaped material carrying the slime preventing/removing agent, and fixing said bag or said flexible tape-shaped material on a surface or an upper surface of a slime contaminated wall, and a solution of the slime preventing/removing agent spreads over the wall.

* * * * *